(12) United States Patent
Kishi

(10) Patent No.: US 10,245,114 B2
(45) Date of Patent: Apr. 2, 2019

(54) MEDICAL MANIPULATOR

(71) Applicant: OLYMPUS CORPORATION, Tokyo (JP)

(72) Inventor: Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 308 days.

(21) Appl. No.: 15/049,467

(22) Filed: Feb. 22, 2016

(65) Prior Publication Data

US 2016/0166347 A1 Jun. 16, 2016

Related U.S. Application Data

(63) Continuation of application No. PCT/JP2014/071488, filed on Aug. 15, 2014.

(30) Foreign Application Priority Data

Aug. 26, 2013 (JP) .................................. 2013-175044

(51) Int. Cl.
*B25J 17/00* (2006.01)
*B25J 17/02* (2006.01)
(Continued)

(52) U.S. Cl.
CPC .............. *A61B 34/71* (2016.02); *A61B 34/30* (2016.02); *A61B 34/37* (2016.02); *A61B 2034/305* (2016.02); *A61B 2034/715* (2016.02)

(58) Field of Classification Search
CPC ......... A61B 34/71; A61B 34/30; A61B 34/37; A61B 2034/305; A61B 2034/715
See application file for complete search history.

(56) References Cited

U.S. PATENT DOCUMENTS

| 5,807,377 A | 9/1998 | Madhani et al. |
| 5,876,325 A | 3/1999 | Mizuno et al. |

(Continued)

FOREIGN PATENT DOCUMENTS

| JP | H07-136173 A | 5/1995 |
| JP | H08-173441 A | 7/1996 |

(Continued)

OTHER PUBLICATIONS

International Search Report dated Nov. 25, 2014 issued in PCT/JP2014/071488.

(Continued)

*Primary Examiner* — Jake Cook
(74) *Attorney, Agent, or Firm* — Scully, Scott, Murphy & Presser, P.C.

(57) ABSTRACT

A medical manipulator includes a treatment part; a joint part that is provided at an end of the treatment part and configured to be operated through turning of a rotating body; an elongated member that has a longitudinal axis and is connected to the end of the joint part opposite to a side where the end effector is provided; a driving part that is provided on a proximal side of the elongated member and is configured to supply a driving force for operating the second coupling member or the like; a driving wire member that is connected at least to the second coupling member of the joint part and is stretched between the second coupling member and the elongated member; and a wire relaxation mechanism that is configured to relax the driving wire by changing the path length of the driving wire.

18 Claims, 25 Drawing Sheets

(51) Int. Cl.
   *B25J 18/00*     (2006.01)
   *A61B 34/00*     (2016.01)
   *A61B 34/30*     (2016.01)
   *A61B 34/37*     (2016.01)

(56) References Cited

U.S. PATENT DOCUMENTS

| | | |
|---|---|---|
| 2004/0118440 A1 | 6/2004 | Sasaki et al. |
| 2004/0199147 A1 | 10/2004 | Nishizawa et al. |
| 2008/0183193 A1* | 7/2008 | Omori ................... A61B 17/29 606/130 |
| 2009/0030449 A1 | 1/2009 | Kawai et al. |
| 2009/0031842 A1 | 2/2009 | Kawai et al. |
| 2009/0112229 A1 | 4/2009 | Omori et al. |
| 2010/0228283 A1 | 9/2010 | Jinno |

FOREIGN PATENT DOCUMENTS

| | | |
|---|---|---|
| JP | 2004-105283 A | 4/2004 |
| JP | 2004-122286 A | 4/2004 |
| JP | 2009-028156 A | 2/2009 |
| JP | 2009-028425 A | 2/2009 |
| JP | 2009-106606 A | 5/2009 |
| JP | 5042738 B2 | 10/2012 |

OTHER PUBLICATIONS

Extended Supplementary European Search Report dated Mar. 16, 2017 in European Patent Application No. 14 84 0515.2.

\* cited by examiner

MEDICAL MANIPULATOR

This application is a continuation application based on a PCT International Application No. PCT/JP2014/071488, whose priority is claimed on Japanese Patent Application No. 2013-175044, filed on Aug. 26, 2013. The contents of both the PCT International Application and the Japanese Patent Application are incorporated herein by reference.

BACKGROUND OF THE INVENTION

Field of the Invention

The present invention relates to a medical manipulator.

Description of Related Art

In the related art, apparatuses adopting various configurations and control methods are known as medical manipulators. For example, a medical manipulator used for master/slave type medical systems including a master manipulator manipulated by an operator and a slave manipulator that operates on the basis of a signal issued from the master manipulator are known as the medical manipulators. End effectors, such as a treatment part for performing a treatment on a treatment target region through remote manipulation, are attached to such medical manipulators.

Since such medical manipulators are inserted into a patient's body cavity and repeatedly used, cleaning, sterilization processing, and the like after use are indispensable.

For example, Japanese Patent Publication No. 5042738 describes an apparatus having a working part in which a distal operation part, having an end effector in which an opening/closing operation is possible, is turnably coupled to the distal end of a tubular coupling shaft, as a medical manipulator that can be used for such a master/slave type medical system.

At least a portion of the distal operation part of the medical manipulator given in Japanese Patent Publication No. 5042738 is covered with a cover, and holes for allowing a cleaning agent to flow therethrough to clean the inside of the distal operation part are provided at sides of this cover. A turning joint mechanism obtained by combining a rotating body wire-driven on a proximal side, and a driven rotating body gear-coupled to the rotating body is adopted as a turning mechanism of the distal operation part.

SUMMARY OF THE INVENTION

According to a first aspect of the present invention, a medical manipulator includes an end effector; a joint part that is provided at an end of the end effector and configured to be operated through turning of a rotating body; an elongated part that has a longitudinal axis and is connected to an end of the joint part opposite to a side where the end effector is provided; a driving part that is provided on a proximal side of the elongated part and configured to supply a driving force for operating the rotating body; a driving wire member that is connected at least to the rotating body of the joint part and is stretched between the rotating body and the elongated part; and a wire relaxation mechanism that is configured to relax the driving wire member by changing the path length of the driving wire member.

According to a second aspect of the present invention, in the medical manipulator according to the first aspect, the wire relaxation mechanism may be arranged at a proximal end of the elongated part, and the driving wire member is encapsulated, and the path length of the driving wire member between the rotating body and the driving part may be changed by extending and retracting the wire relaxation mechanism in a longitudinal direction of the elongated part.

According to a third aspect of the present invention, in the medical manipulator according to the second aspect, the wire relaxation mechanism may include a male screw part that is provided on the proximal side of the elongated part; and a position-adjusting part that is disposed between the elongated part and the driving part and has a female screw part corresponding to the male screw part, and the wire relaxation mechanism may be extended and retracted in the longitudinal direction of the elongated part by twisting the position-adjusting part.

According to a fourth aspect of the present invention, in the medical manipulator according to any one of the first aspect to the third aspect, the wire relaxation mechanism may further include a stopper part for fixing the path length of the driving wire member not to be changed.

According to a fifth aspect of the present invention, in the medical manipulator according to the fourth aspect, the stopper part may include a stopper member that is disposed to be movable forward and backward on a movement path relative to the driving part of the elongated part when the wire relaxation mechanism is extended and retracted; an elastic member that biases the stopper member in a direction in which the stopper member advances to the movement path; and a manipulation part that is configured to release the biasing of the elastic member.

According to a sixth aspect of the present invention, in the medical manipulator according to any one of the first aspect to the fifth aspect, the driving wire member may be wound around and connected to the rotating body, and the distance between the periphery of the rotating body and the driving wire member may increase when the driving wire member is relaxed by the wire relaxation mechanism.

According to a seventh aspect of the present invention, in the medical manipulator according to any one of the first aspect to the sixth aspect, the joint part may include a unit joint that is coupled to one end of the elongated part in a direction along the longitudinal axis, the unit joint may include a proximal-side support having a first turning shaft that is provided on the elongated part side and extends in a direction intersecting the longitudinal axis at the one end, and a first guide part that has the first turning shaft as a turning shaft; a distal-side turning body having a second turning shaft that is provided on the end effector side to face the proximal-side support and extends parallel to the first turning shaft, and a second guide part that has the second turning shaft as a turning shaft; and a coupling member that is the rotating body that holds the first turning shaft and the second turning shaft, respectively, and is configured to be turnable around the first turning shaft; and the joint part further includes a guide wire that is connected to or engaged with the proximal-side support of the joint part and the distal-side turning body that is the rotating body, the guide wire having an end fixed to the elongated part, and guiding the turning of the distal-side turning body when the joint part operates.

According to an eighth aspect of the present invention, in the medical manipulator according to the seventh aspect, the first guide part may further include a first pulley, the second guide part may further include a second pulley that is configured to abut against or engage with the first guide part, and is configured to guide rolling of the end effector along the track of the first guide part, and the first pulley may be configured to guide rolling of the second pulley centered on the first turning shaft.

According to a ninth aspect of the present invention, in the medical manipulator according to the seventh aspect or the eighth aspect, the coupling member may be capable of changing an inter-axial between the first turning shaft and the second turning shaft to the state of a first inter-axial distance at which the first guide part and the second guide part abut against or engage with each other and the state of a second inter-axial distance at which the inter-axial distance is longer than the first inter-axial distance, the guide wire may be wound around the distal-side turning body and the proximal-side support so that tension is generated in the state of the first inter-axial distance and the guide wire is relaxed in the state of the second inter-axial distance, and the wire relaxation mechanism may adjust the relative positions of the elongated part and the driving part, thereby forming the state of the second inter-axial distance to relax at least the guide wire.

According to a tenth aspect of the present invention, in the medical manipulator according to any one aspect of the seventh aspect to the ninth aspect, the guide wire may be connected or engaged such that the guide wire cannot be separated from at least one of the driving part and the distal-side turning body.

According to an eleventh aspect of the present invention, in the medical manipulator according to any one of the seventh aspect to the ninth aspect, the guide wire may be connected or engaged at a predetermined position of at least one of the driving part and the distal-side turning body.

According to a twelfth aspect of the present invention, in the medical manipulator according to any one of the seventh aspect to the eleventh aspect, the first guide part and the second guide part may be constituted of a set of gear members, a first wire insertion part capable of stretching the guide wire between axial centers may be formed in the first turning shaft, a second wire insertion part capable of stretching the guide wire between axial centers may be formed in the second turning shaft, and the guide wire may be inserted through the first wire insertion part and the second wire insertion part and may be connected to or engaged with the driving part and the distal-side turning body.

According to a thirteenth aspect of the present invention, in the medical manipulator according to any one of the seventh aspect to the twelfth aspect, the coupling member may include a fixing pulley that has a pulley groove for winding the driving wire member on a circumference coaxial with the first turning shaft, and the driving part may include a driving pulley that engages with the driving wire member and moves the driving wire member forward and backward in the direction along the longitudinal axis.

According to a fourteenth aspect of the present invention, in the medical manipulator according to any one of the seventh aspect to the thirteenth aspect, the joint part may include a first unit joint and a second unit joint that are coupled to one end of the elongated part in the direction along the longitudinal axis, the first unit joint may be coupled to the one end of the elongated part, and the second unit joint couples the distal-side turning body of the first unit joint and the end effector, and the first unit joint and the second unit joint may be coupled together in a positional relationship in which axis directions of the first turning shaft and the second turning shaft of the second unit joint are orthogonal at positions twisted from axis directions of the first turning shaft and the second turning shaft of the first unit joint.

DETAILED DESCRIPTION OF THE INVENTION

Figure 1:
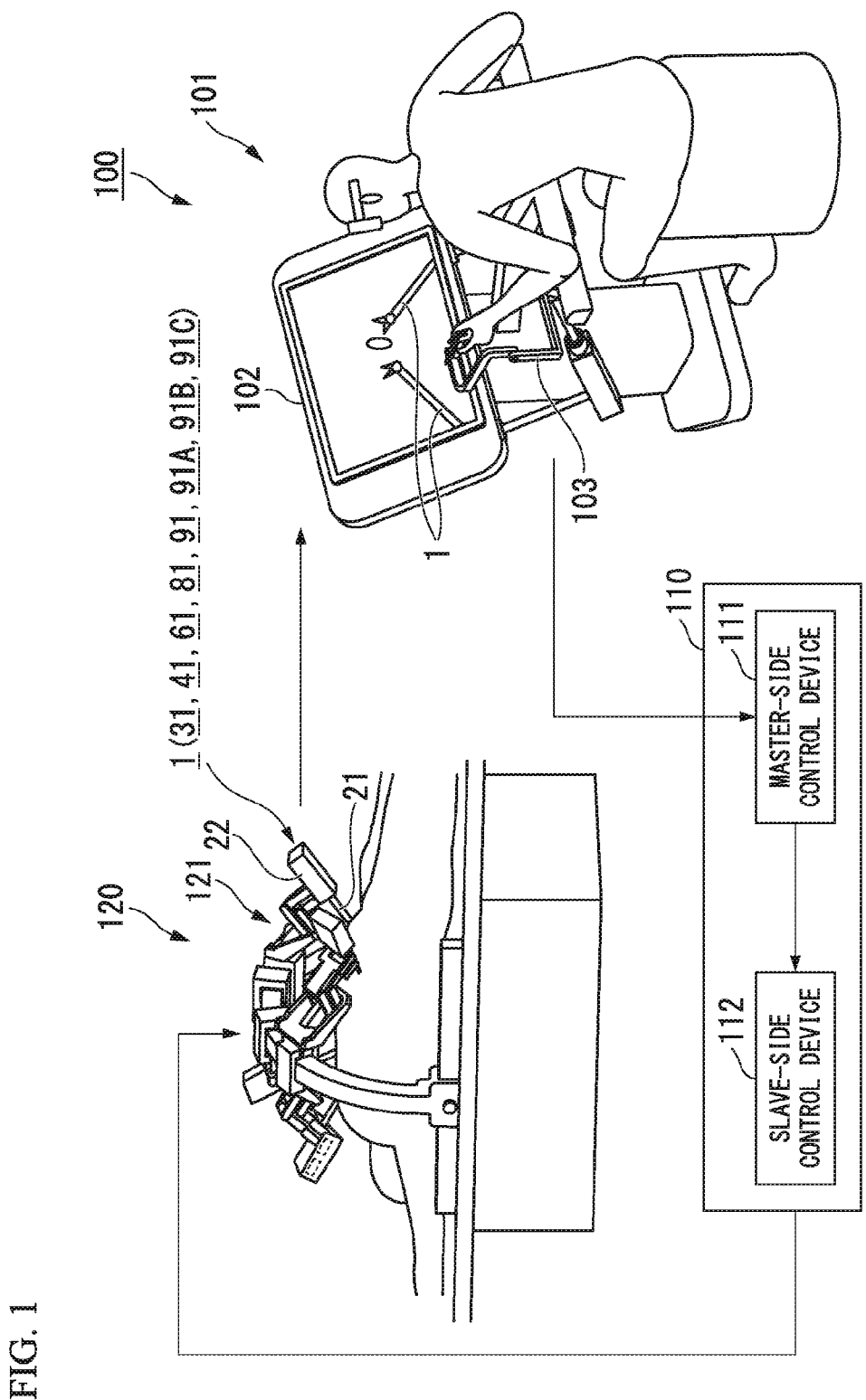
FIG. 1 is a schematic configuration view of a medical system including a medical manipulator of a first embodiment of the invention.

Hereinafter, embodiments of the invention will be described with reference to the accompanying drawings. In all the drawings, even in the case of different embodiments, the same reference numerals will be given to the same or equivalent members, and common description will be omitted.

First Embodiment

A medical manipulator of a first embodiment of the invention will be described.

Figure 2:
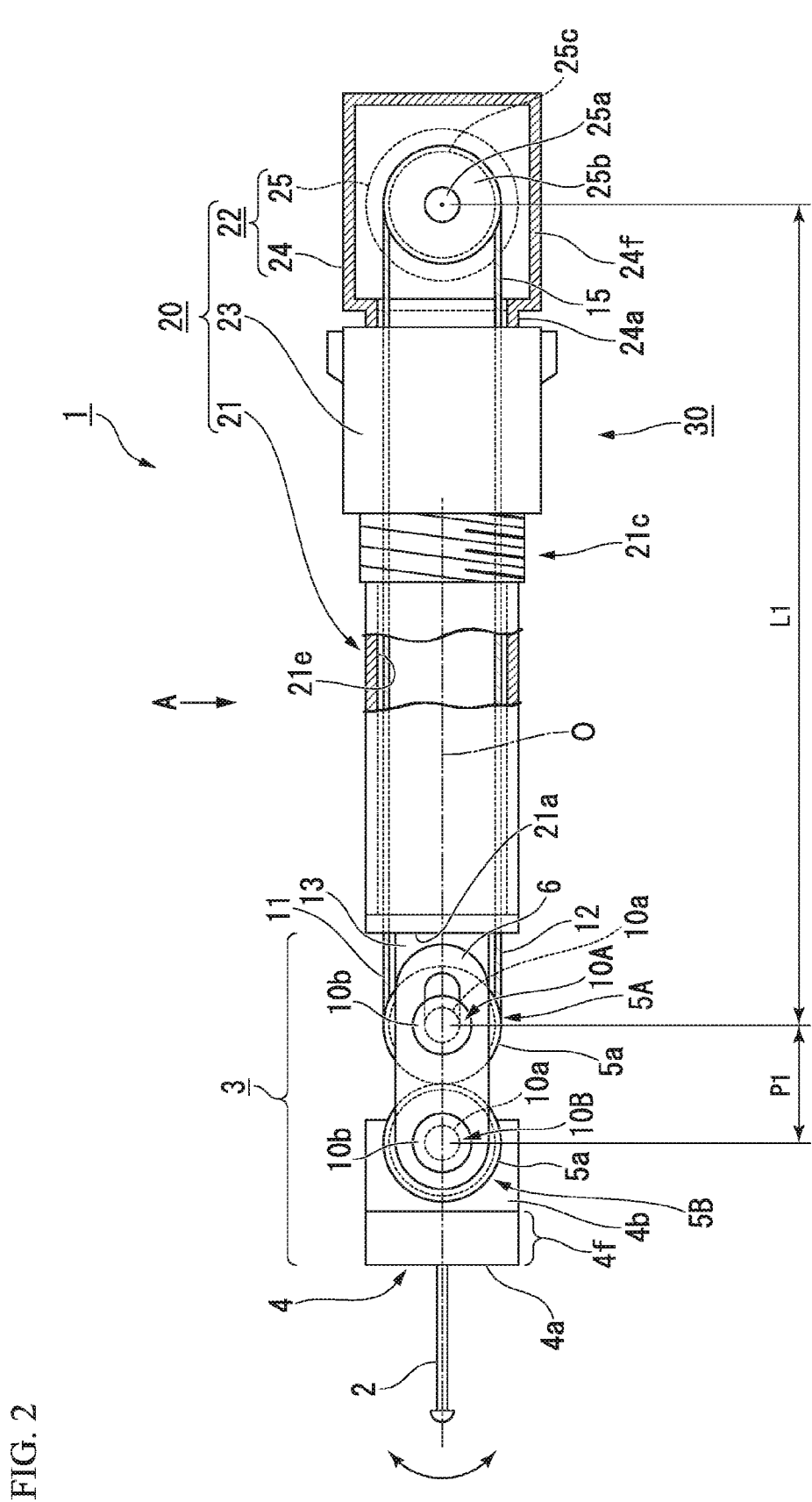
FIG. 2 is a schematic front view illustrating the configuration of the medical manipulator of the first embodiment of the invention.
Figure 3:
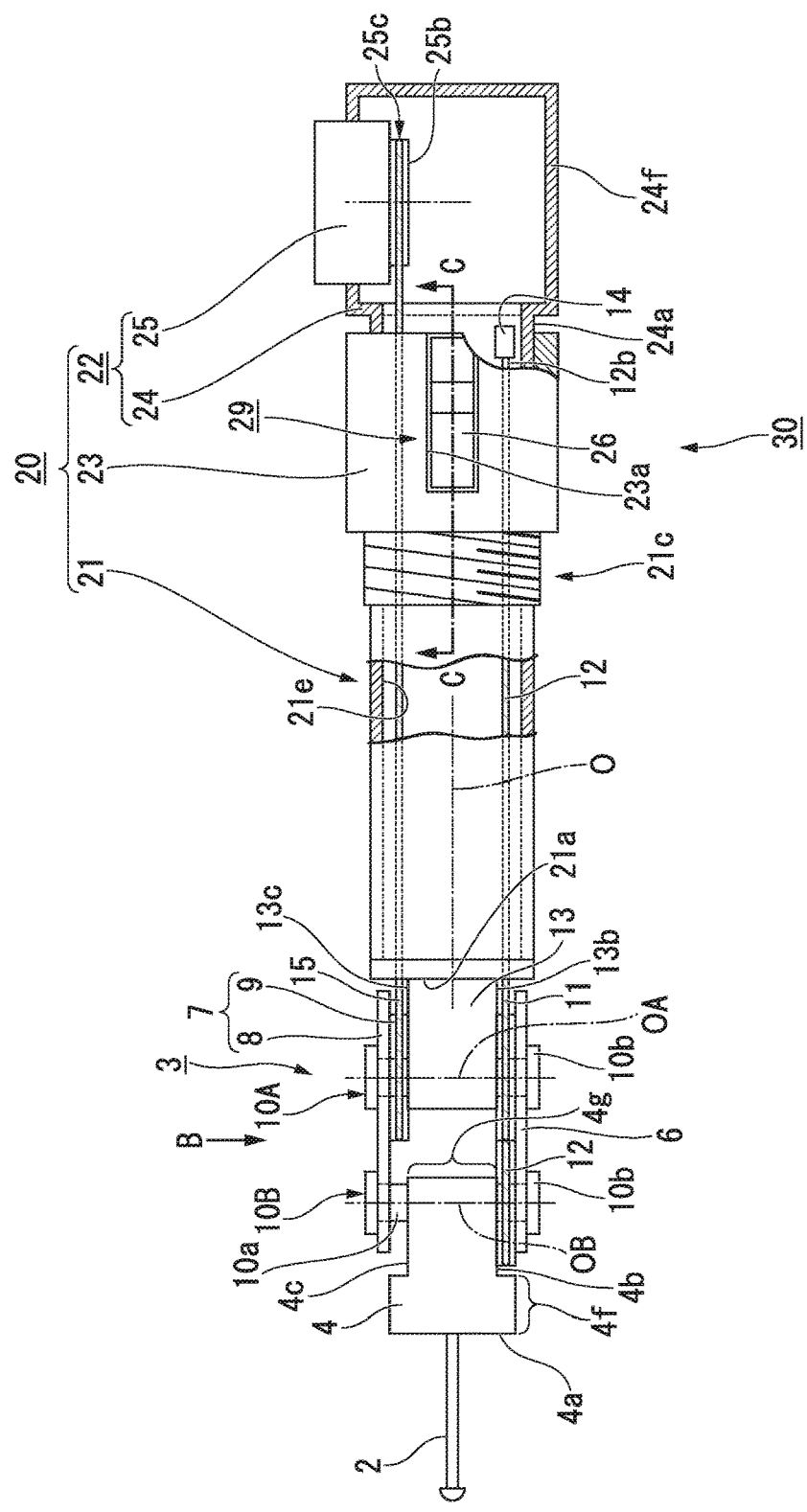
FIG. 3 is a view as seen from A in FIG. 2.
Figure 4:
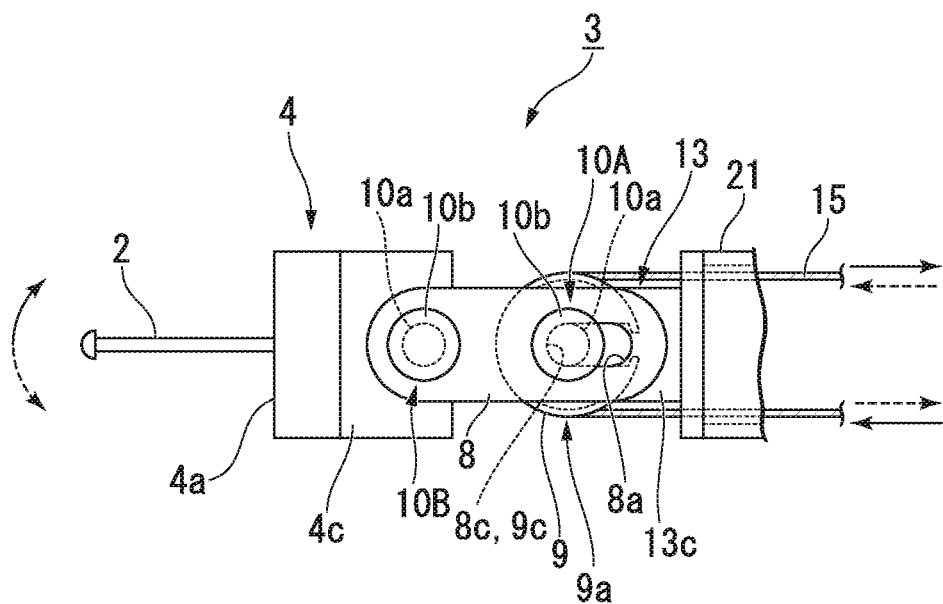
FIG. 4 is a view as seen from B in FIG. 3.
Figure 5:
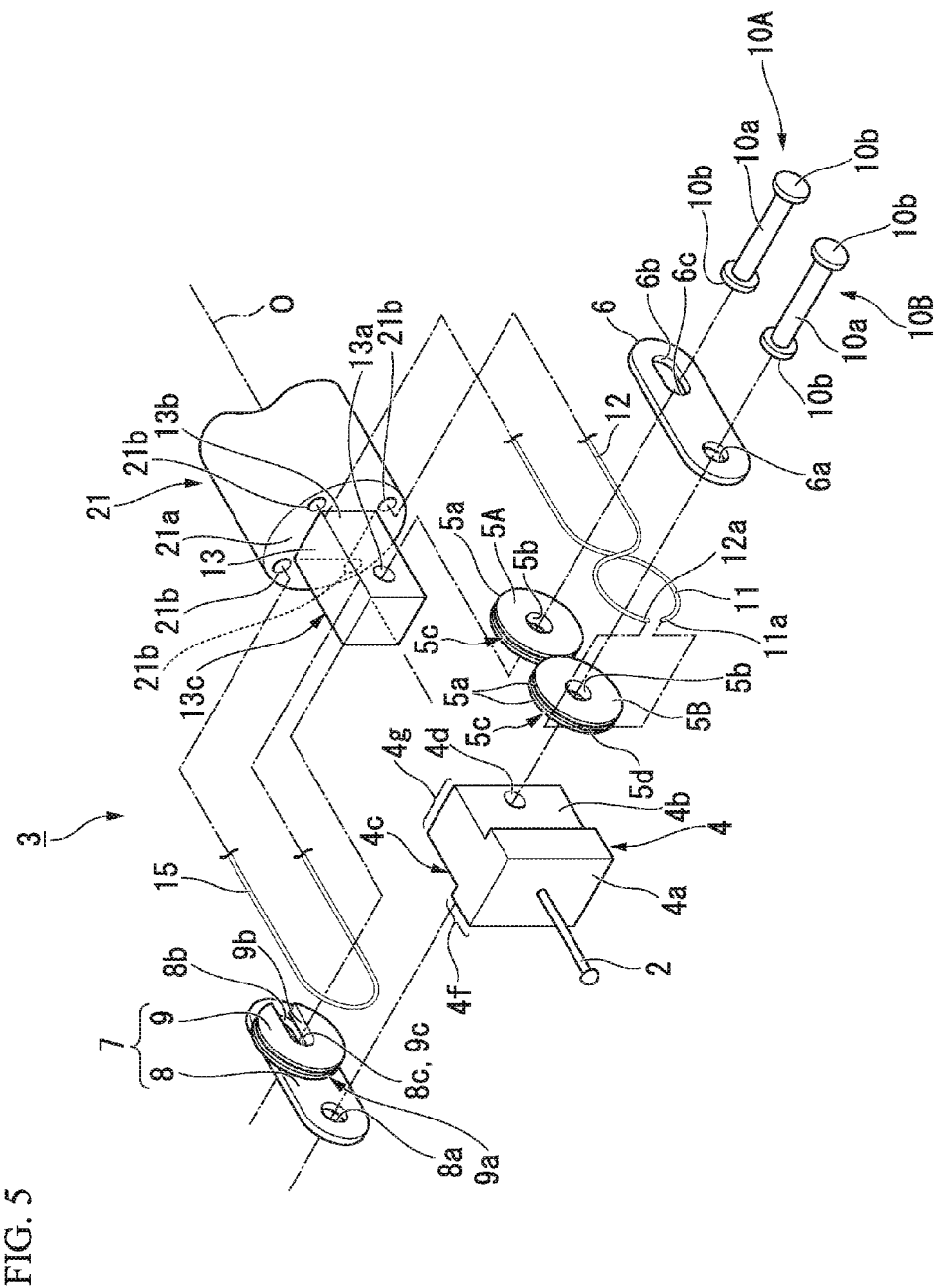
FIG. 5 is a schematic exploded perspective view illustrating the configuration of a joint part of the medical manipulator of the first embodiment of the invention.
Figure 6:
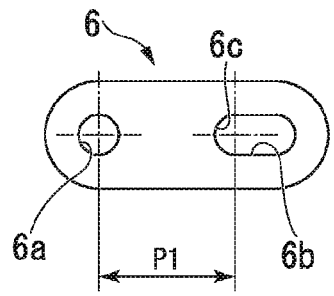
FIG. 6 is a schematic front view illustrating a first coupling member of the joint part of the medical manipulator of the first embodiment of the invention.
Figure 7A:
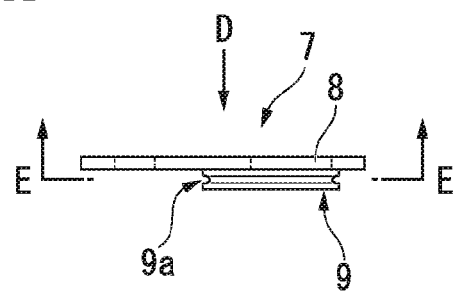
FIG. 7A is a schematic side view illustrating a second coupling member of the joint part of the medical manipulator of the first embodiment of the invention.
Figure 7B:
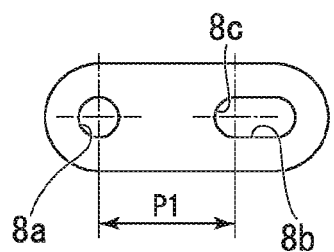
FIG. 7B is a view as seen from D of FIG. 7A.
Figure 7C:
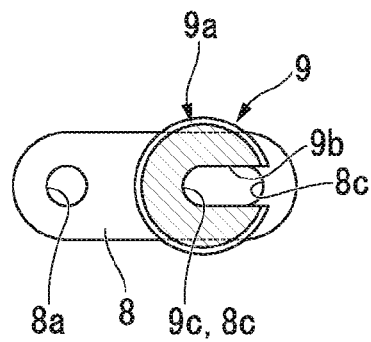
FIG. 7C is an E-E sectional view of FIG. 7A.
Figure 8:
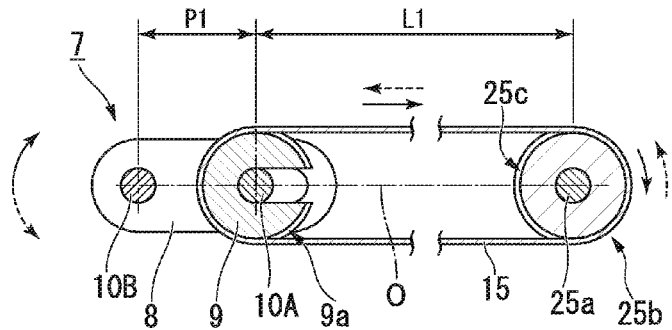
FIG. 8 is a schematic view illustrating wiring of a driving wire member of the medical manipulator of the first embodiment of the invention.
Figure 9A:
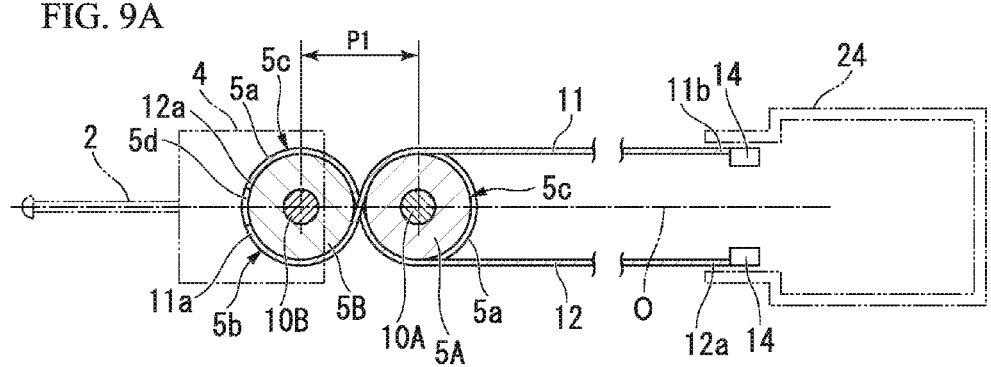
FIG. 9A is a schematic view illustrating wiring of a guide wire of the medical manipulator of the first embodiment of the invention.
Figure 9B:
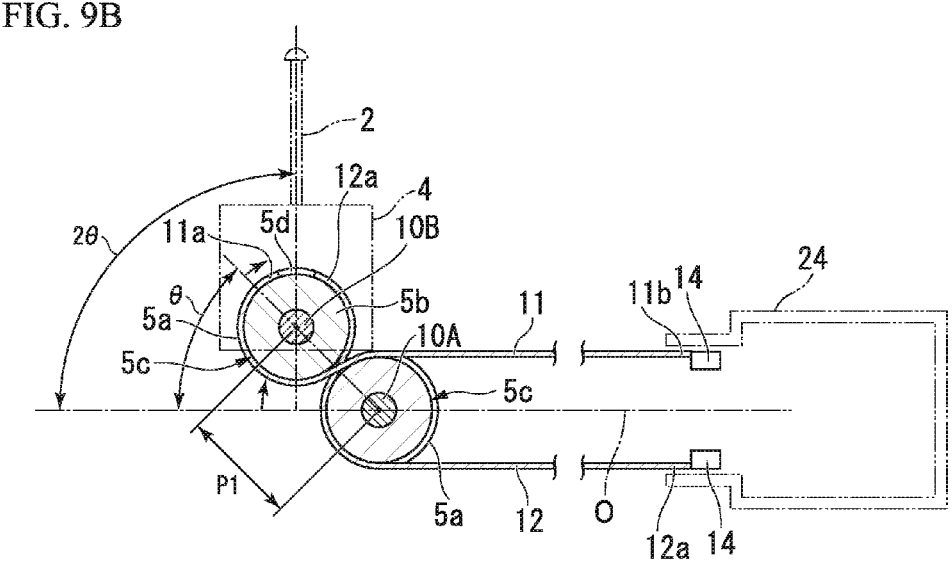
FIG. 9B is a schematic view illustrating the wiring of the guide wire of the medical manipulator of the first embodiment of the invention.
Figure 10A:
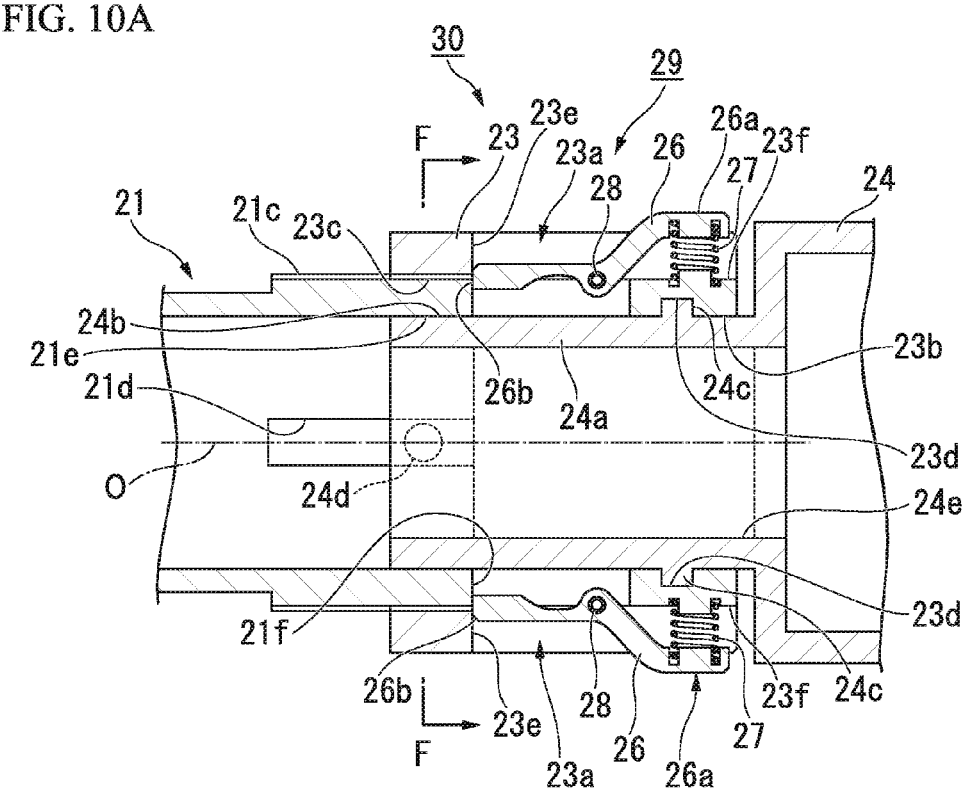
FIG. 10A is a C-C sectional view in FIG. 3.
Figure 10B:
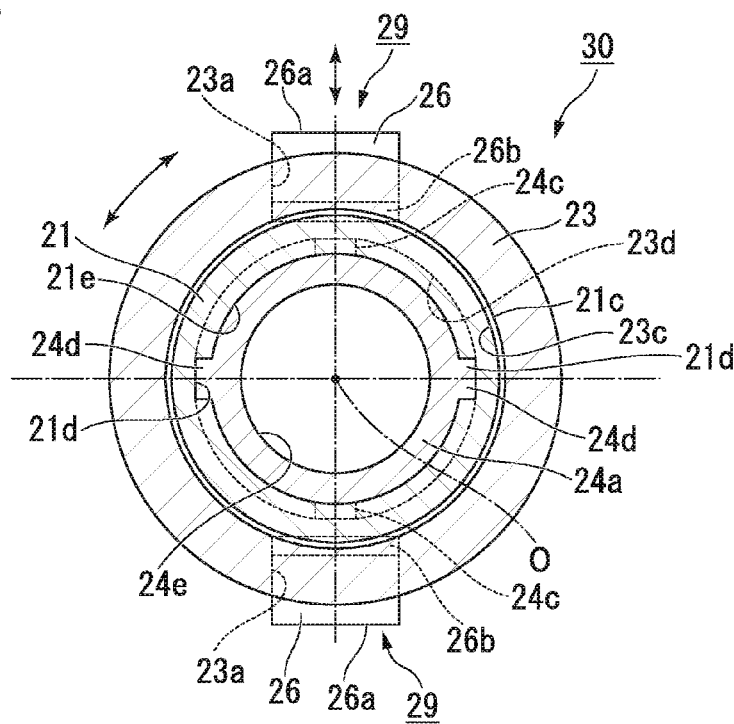
FIG. 10B is an F-F sectional view in FIG. 10A.

FIG. 1 is a schematic configuration view of a medical system including the medical manipulator of the first embodiment of the invention. FIG. 2 is a schematic front view illustrating the configuration of the medical manipulator of the first embodiment of the invention. FIG. 3 is a view as seen from A in FIG. 2. FIG. 4 is a view as seen from B in FIG. 3. FIG. 5 is a schematic exploded perspective view illustrating the configuration of a joint part of the medical manipulator of the first embodiment of the invention. FIG. 6 is a schematic front view illustrating a first coupling member of the joint part of the medical manipulator of the first embodiment of the invention. FIG. 7A is a schematic side view illustrating a second coupling member of the joint part of the medical manipulator of the first embodiment of the invention. FIGS. 7B and 7C are a view as seen from D in FIG. 7A and an E-E cross-sectional view in FIG. 7A. FIG. 8 is a schematic view illustrating wiring of a driving wire member of the medical manipulator of the first embodiment of the invention. FIGS. 9A and 9B are schematic views illustrating wiring of a guide wire of the medical manipulator of the first embodiment of the invention. FIG. 10A is a C-C sectional view in FIG. 3. FIG. 10B is an F-F sectional view in FIG. 10A.

As illustrated in FIG. 1, a medical manipulator 1 of the present embodiment is attached to a medical system 100 as a portion of the medical system 100.

First, the configuration of the medical system 100 will be described. The medical system 100 includes a master manipulator 101, a control device 110, and a slave manipulator 120.

The slave manipulator 120 includes a robot arm 121 and the medical manipulator 1.

The master manipulator 101 functions as a master that transmits a surgeon's manipulation motion to the slave manipulator 120, and includes a master display part 102, such as a liquid crystal display device, and a manipulation part 103 that is grasped and manipulated by a surgeon. A manipulation performed on the manipulation part 103 of the master manipulator 101 is input to the control device 110.

The control device 110 has a master-side control device 111 that receives the input from the master manipulator 101, and a slave-side control device 112 that outputs a driving signal to the slave manipulator 120.

In the master-side control device 111, a manipulation command for operating the slave manipulator 120 is generated on the basis of the input from the master manipulator 101, and is output to the slave-side control device 112.

In the slave-side control device 112, a driving signal for driving the slave manipulator 120 is generated on the basis of the manipulation command issued from the master-side control device 111, and is output to the slave manipulator 120.

The slave manipulator 120 has the robot arm 121 that operates according to the driving signal from the slave-side control device 112, and the medical manipulator 1 is attached to the robot arm 121. A treatment instrument, an endoscope apparatus, or the like for performing a surgical operation in addition to the medical manipulator 1 can also be further attached to the slave manipulator 120.

Next, the configuration of the medical manipulator 1 will be described. The medical manipulator 1 is a medical instrument for performing a treatment on a treatment target region, and has a long and narrow shaft-like outer shape at least on a distal side close to the treatment target region.

In the following, an end closer to a treatment target region at the time of use in a longitudinal direction of the medical manipulator 1 is referred to as a distal end, and an end opposite to the distal end is referred to as a proximal end. Unless particularly mentioned, with respect to the arrangement of members between the proximal end and the distal end and the relative positional relationship in the arranged members, a side where these members are relatively near the distal end is referred to as a "distal side", and a side where these members are relatively near the proximal end is referred to as a "proximal side".

As illustrated in FIGS. 2 to 4, the medical manipulator 1 includes a treatment part (end effector) 2, a joint part 3, and a body part 20 in this order from the distal side toward the proximal side.

The treatment part 2 is a device section that performs treatment on a treatment target region, and is coupled to the distal end of the joint part 3.

The joint part 3 is a device section for performing a turning motion of the treatment part 2 with respect to the longitudinal axis of a device defined by the body part 20 as will be described below, and couples the proximal side of the treatment part 2 and the distal side of the body part 20.

The body part 20 is a device section that houses therein a driving source that generates a driving force that drives the joint part 3, and a driving force transmission member that transmits the driving force generated by the driving source to the joint part 3, and has a tubular outer shape as a whole.

In the present embodiment, as illustrated in FIGS. 2 and 3, a case where the driving source is constituted of a drive motor 25 including a driving shaft 25a and a driving pulley 25b fixed to the driving shaft 25a will be described as an example.

The drive motor 25 consists of, for example, a DC motor, and is electrically connected to the slave-side control device 112 (refer to FIG. 1) outside the medical manipulator 1 by a wiring line that is not illustrated. The drive motor 25 and the driving pulley 25b may be detachably configured.

As the driving force transmission member corresponding to the drive motor 25, a driving wire 15 (driving wire member) to be described below is adopted.

A bottomed cylindrical elongated member 21 (elongated part), which has a cylindrical outer shape and opens on the proximal side with a distal end surface 21a as a bottom surface, is arranged on the distal side of the body part 20.

A central axis of the outer shape of the elongated member 21 defines a longitudinal axis O of the body part 20. In the present embodiment, since the elongated member 21 is a hard member, the longitudinal axis O is a straight line. However, the elongated member may be a soft part in which an outer shape is cylindrical and has flexibility.

In the medical manipulator 1, the joint part 3 is bendable as will be described below, and the length thereof in a direction along the longitudinal axis O of the body part 20 is changeable. The length of the body part 20 is changed by changing the distance between the elongated member 21 and a proximal-side device section 22 (driving part) to be described below. Accordingly, it is possible to perform switching between a drivable state where driving of the joint part 3 is possible, and a relaxation state where driving of the driving wire 15 (to be described below) to be used for driving in the joint part 3 is relaxed and the driving of the joint part is impossible.

Thus, in the following description, unless particularly mentioned in describing the positional relationship of the respective members in the drivable state, as illustrated in FIGS. 2 to 4, description will be made on the basis of a state where the joint part 3 does not turn with respect to the longitudinal axis O.

As the configuration of the treatment part 2, a suitable configuration can be adopted according to a required treatment. For example, members that extend in the shape of a rod, a hook, or the like in order to hold down living body tissue, tube members, such as an injection needle, grasping forceps obtained by combining a plurality of treatment tool pieces, members that cut or ablate living body tissue through energization, high-intensity focused ultrasound therapy (HIFU) probes, or the like can be exemplified.

In this way, the treatment part 2 may be any kind of instrument to be used for treatment, such as a surgical operation. For example, members that do not move may be used, movable members may be used, or members which an electric current is applied may be used.

In the present embodiment, a high-frequency knife that extends in the shape of a rod along the longitudinal axis O of the medical manipulator 1 is illustrated as an example. In the case of such a high-frequency knife, a well-known electrical wiring line for energization is connected to a proximal end of the treatment part 2. This electrical wiring line is connected to a power source outside the device through the joint part 3 and the body part 20. However, in the present embodiment, in order to make the configuration of the principal parts easily seen, illustration of the electrical wiring line, a hole through which the electrical wiring line is inserted, and the like are omitted.

The joint part 3 can provide one or more unit joints that constitute a suitable turning joint and a suitable bending joint of the body part 20. In the present embodiment, a case where the joint part consists of one bending joint that turns the treatment part 2 in the direction of a circle arrow within the paper surface of FIG. 2 will be described as an example.

The joint part 3 includes a proximal-side support 13, a distal-side turning body 4, a first coupling member (coupling member) 6, a proximal-side pulley (a first pulley or a first guide part) 5A, a distal-side pulley (a second pulley or a second guide part) 5B, and a second coupling member (a rotating body or a coupling member) 7.

A proximal end of the proximal-side support 13, as illustrated in FIG. 5, is a member that is coupled to the distal end surface 21a of the elongated member 21, extends along the longitudinal axis O, and has a rectangular parallelepiped shape. The proximal-side support 13 includes a first side surface 13b and a second side surface 13c that face each other with the longitudinal axis O interposed therebetween. A turning shaft-holding part 13a constituted of a through-hole that turnably holds a first turning shaft 10A in a direction orthogonal to the longitudinal axis O is provided between the first side surface 13b and the second side surface 13c.

In the present embodiment, as an example, the first turning shaft 10A is constituted of a shaft member having a columnar shaft part 10a that is turnably fitted to the turning shaft-holding part 13a, and retaining parts 10b that are provided at both ends of the shaft part 10a. The retaining parts 10b can be formed by, for example, rivets, screw members, or the like that are fixed to both the ends of the shaft part 10a. Additionally, the retaining part 10b at one end may be formed integrally with the shaft part 10a.

The length of the proximal-side support 13 along the longitudinal axis O and the position of the turning shaft-holding part 13a are set in a dimensional relationship in which these members do not interfere with a distal end of the elongated member 21 when the proximal-side pulley 5A, the first coupling member 6, and the second coupling member 7 to be described below are assembled.

As illustrated in FIG. 5, the treatment part 2 is fixed to the distal side of the distal-side turning body 4. The distal-side turning body 4 has a rectangular first plate-shaped part 4f in which a distal end surface 4a consisting of a planar surface orthogonal to an extending direction of the treatment part 2 is formed, and a second plate-shaped part 4g that is erected from the back side of the distal end surface 4a in the first plate-shaped part 4f. Accordingly, the outer shape of the distal-side turning body 4 is a shape in which a T-shaped section (refer to FIG. 3) extends in one direction orthogonal to the longitudinal axis O.

The second plate-shaped part 4g has the same thickness as the thickness between the first side surface 13b and the second side surface 13c of the proximal-side support 13, and includes a first side surface 4b and a second side surface 4c that face each other with the longitudinal axis O interposed therebetween. In the drivable state (refer to FIG. 3), the first side surface 4b is aligned with the first side surface 13b of the proximal-side support 13 on the same plane and the second side surface 4c is aligned with the second side surface 13c of the proximal-side support 13 on the same plane.

A turning shaft-holding part 4d constituted of a through-hole that turnably holds a second turning shaft 10B in the direction orthogonal to the longitudinal axis O is provided between the first side surface 4b and the second side surface 4c. The shaft diameter of the second turning shaft 10B may be different from that of the first turning shaft 10A. However, in the present embodiment, as an example, the second turning shaft 10B is arranged coaxially with the first turning shaft 10A, and adopts the same shaft member as the first turning shaft 10A.

The length of the second plate-shaped part 4g along the longitudinal axis O and the position of the turning shaft-holding part 4d are set in a dimensional relationship in which these members do not interfere with the first plate-shaped part 4f when the distal-side pulley 5B, the first coupling member 6, and the second coupling member 7 to be described below are assembled.

The first coupling member 6, as illustrated in FIG. 6, is a plate-shaped member that has an oval outer shape, and a circular hole 6a for a bearing and a sliding hole 6b for a bearing pass through the first coupling member at a central part in a lateral direction.

The circular hole 6a for a bearing is constituted of a circular hole that holds the second turning shaft 10B so that the relative rotation of the second turning shaft 10B around its axis is possible, and is formed near one end of the first coupling member 6 in the longitudinal direction.

The sliding hole 6b for a bearing is an oval hole in which a centerline in the lateral direction passes through the center of the circular hole 6a for a bearing and which extends along the longitudinal direction of the first coupling member 6. The width of the sliding hole 6b for a bearing of the lateral direction is slightly greater than the external diameter of the shaft part 10a of the first turning shaft 10A in order to hold the shaft part 10a of the first turning shaft 10A in a slidingly movable manner along the longitudinal direction of the sliding hole 6b for a bearing.

A bearing part 6c consisting of a curved surface, which holds the shaft part 10a of the first turning shaft 10A so that the relative rotation of the first turning shaft 10A around its axis is possible when the first turning shaft 10A has abutted and which has a semicircular cross-sectional shape, is formed at the end of the sliding hole 6b for a bearing that faces the circular hole 6a for a bearing in the longitudinal direction. The size of the center distance between the center of the circular hole 6a for a bearing and the center of the bearing part 6c is P1.

As illustrated in FIGS. 2 and 5, the proximal-side pulley 5A is arranged at a position coaxial with the first turning shaft 10A, and the distal-side pulley 5B is arranged at a position coaxial with the second turning shaft 10B. The proximal-side pulley 5A and the distal-side pulleys 5B are a set of pulleys made relatively rollable along their respective pitch circles by winding a wire 11 (guide wire) for a first guide and a wire 12 (guide wire) for a second guide around on the outer peripheral sides thereof in the drivable state.

The distal-side pulley 5B is fixed to the first side surface 4b of the distal-side turning body 4 by fixing means (not illustrated), for example, screw fastening, crimping, press-fitting, welding, deposition, or the like, or is molded integrally with the distal-side turning body 4.

In the present embodiment, the proximal-side pulley 5A is turnably assembled to the proximal-side support 13 and the first turning shaft 10A.

However, the proximal-side pulley 5A can be fixed to the first side surface 13b of the proximal-side support 13 by suitable fixing means, or can be molded integrally with the proximal-side support 13.

If the wire 11 for a first guide and the wire 12 for a second guide can be engaged with the proximal-side pulley 5A and the distal-side pulley 5B without slipping, the type of the wires is not particularly limited. As examples of the wires suitable as the wire 11 for a first guide, and the wire 12 for a second guide, for example, stainless steel wires can be adopted.

As illustrated in FIGS. 2 and 5, the proximal-side pulley 5A includes pulley grooves 5c for winding the wire 11 for a first guide and the wire 12 for a second guide, a through-hole 5b through which the shaft part 10a of the first turning shaft 10A is insertable and which is formed coaxially with a pitch circle, and an outer peripheral surface 5a that is formed coaxially with the pitch circle.

The proximal-side pulley 5A is arranged so as to be sandwiched between the first side surface 13b of the proximal-side support 13 and the first coupling member 6 at a position where the pitch circle of the pulley groove 5c becomes coaxial with the first turning shaft 10A in a state where the shaft part 10a of the first turning shaft 10A has been inserted through the through-hole 5b.

The distal-side pulley 5B includes pulley grooves 5c, a through-hole 5b, and an outer peripheral surface 5a that are the same as those of the proximal-side pulley 5A.

However, the distal-side pulley 5B is different from the proximal-side pulley 5A in that the shaft part 10a of the second turning shaft 10B is inserted through the through-hole 5b of the distal-side pulley 5B, and wire-fixing parts 5d that fix a distal end 11a of the wire 11 for a first guide and a distal end 12a of the wire 12 for a second guide in a mutually facing manner are fixed on the pulley grooves 5c.

In addition, below is an example of the wire-fixing parts 5d being provided at the distal-side pulley 5B. For example, the wire-fixing parts 5d can also be provided on the distal-side turning body 4 to which the distal-side pulley 5B has been fixed.

Additionally, in the present embodiment, the external diameters of the outer peripheral surfaces 5a of the proximal-side pulley 5A and the distal-side pulley 5B have sizes obtained by subtracting a wire diameter equivalent to two wires from P1 as an example in consideration of the dimensions of an intersecting part between the wire 11 for a first guide and the wire 12 for a second guide.

The illustration of FIG. 2 and the like is simplified, and the respective outer peripheral surfaces 5a are drawn so as to abut against each other. However, in practice, since the respective outer peripheral surfaces 5a are in the aforementioned dimensional relationship, the outer peripheral surfaces are separated from each other even in the drivable state.

The wire-fixing parts 5d are fixed to an outer peripheral part opposite to the proximal-side pulley 5A with the second turning shaft 10B interposed therebetween in a state where the joint part 3 extends along the longitudinal axis O in the drivable state. The configuration of the wire-fixing parts 5d is not particularly limited if the positions of the distal end 11a of the wire 11 for a first guide and the distal end 12a of the wire 12 for a second guide with respect to the distal-side pulley 5B can be fixed in the drivable state.

For example, the example of fixation by metal members that crimp and fix the distal ends 11a and 12a can be adopted as a configuration in which the positions are fixed in both the drivable state and the relaxation state. Moreover, the distal ends can also be fixed by welding, deposition, screw fastening, or the like.

Additionally, it is also possible to adopt a configuration in which the positions are fixed only in the drivable state. For example, larger-diameter parts used as retainers are formed at the distal ends 11a and 12a, and the example of pipe members having through-holes that allow these wires to be inserted therethrough and having smaller diameters than the respective larger-diameter parts can be adopted as the wire-fixing parts 5d.

In the present embodiment, metal members that crimp the distal ends 11a and 12a are adopted as an example. In this case, the respective distal ends 11a and 12a may be crimped using two wires as the wire 11 for a first guide and the wire 12 for a second guide. Additionally, it is also possible to adopt a configuration in which the portion of the wire 11 for a first guide and the portion of the wire 12 for a second guide extend to both end sides of the wire-fixing parts 5d by constituting the wire 11 for a first guide and the wire 12 for a second guide from one wire and crimping an intermediate part therebetween using a metal member.

As illustrated in FIGS. 3 and 5, the proximal-side pulley 5A and the distal-side pulley 5B having such a configuration are arranged to face the first side surface 13b of the proximal-side support 13 and the first side surface 4b of the distal-side turning body 4, respectively, and are arranged so as to be sandwiched between the first side surface 13b and the first side surface 4b, and the first coupling member 6.

The shaft part 10a of the first turning shaft 10A is inserted through the sliding hole 6b for a bearing of the first coupling member 6 and the through-hole 5b of the proximal-side pulley 5A. The proximal side of the first coupling member 6 is retained in the axial direction by the retaining parts 10b of the first turning shaft 10A.

Additionally, the shaft part 10a of the second turning shaft 10B is inserted through the circular hole 6a for a bearing of the first coupling member 6 and the through-hole 5b of the distal-side pulley 5B. The distal side of the first coupling member 6 is retained in the axial direction by the retaining parts 10b of the second turning shaft 10B.

Accordingly, the first coupling member 6 turnably holds the second turning shaft 10B around the center of the circular hole 6a for a bearing, using the circular hole 6a for a bearing.

Additionally, the first coupling member 6 holds the first turning shaft 10A in a slidingly movable manner along the longitudinal direction of the sliding hole 6b for a bearing in a state where the first turning shaft 10A is kept parallel to the second turning shaft 10B held in the circular hole 6a for a bearing by the sliding hole 6b for a bearing.

Moreover, the first coupling member 6 is able to turnably hold the first turning shaft 10A around the center of the bearing part 6c in the state of a first inter-axial distance where the inter-axial distance between the first turning shaft 10A and the second turning shaft 10B is P1, when the shaft part 10a of the first turning shaft 10A has abutted against the bearing part 6c in the drivable state.

As illustrated in FIGS. 7A, 7B, and 7C, the second coupling member 7 is constituted of a plate-shaped part 8 having the same shape as the first coupling member 6, and a driving force input part 9 that is fixed to one surface of the plate-shaped part 8 or molded integrally with the plate-shaped part 8.

The plate-shaped part 8 includes a circular hole 8a for a bearing having the same shape corresponding to the circular hole 6a for a bearing of the first coupling member 6, at the same position as the circular hole 6a for a bearing. Additionally, the plate-shaped part 8 includes a sliding hole 8b for a bearing having the same shape corresponding to the sliding hole 6b for a bearing of the first coupling member 6, at the same position as the sliding hole 6b for a bearing. Additionally, the plate-shaped part 8 includes a bearing part 8c having the same shape corresponding to the bearing part 6c of the first coupling member 6, at the same position as the bearing part 6c.

For this reason, as illustrated in FIG. 7B, the center distance between the center of the circular hole 8a for a bearing and the center of the bearing part 8c is also P1.

The driving force input part 9 is a plate-shaped part having a pulley groove 9a on a circumference that is coaxial with the central axis of the bearing part 8c, and has a U-shaped groove 9b for a bearing that opens within a range overlapping the circular hole 8a for a bearing.

A bearing part 9c, which is aligned with the bearing part 8c and consists of a curved surface having a semicircular sectional shape, is formed at the groove bottom of the U-shaped groove 9b for a bearing. For this reason, similar to the bearing parts 6c and 8c, the bearing part 9c is able to hold the first turning shaft 10A so that the relative rotation of the first turning shaft 10A around its axis is possible when the first turning shaft 10A has abutted against the bearing part 9c.

The second coupling member 7 having such a configuration, as illustrated in FIGS. 3 and 5, is arranged so that the driving force input part 9 faces the second side surface 13c of the proximal-side support 13 and is retained in the axial direction by the retaining parts 10b of the first turning shaft 10A in a state where the shaft part 10a of the first turning shaft 10A has been inserted through the sliding hole 8b for a bearing.

Additionally, the plate-shaped part 8 is arranged parallel to the second side surface 4c of the distal-side turning body 4 and is retained in the axial direction by the retaining parts 10b of the second turning shaft 10B, in a state where the shaft part 10a of the second turning shaft 10B has been inserted through the circular hole 8a for a bearing.

Accordingly, the second coupling member 7 turnably holds the second turning shaft 10B around the center of the circular hole 8a for a bearing, using the circular hole 8a for a bearing. Additionally, the second coupling member 7 holds the first turning shaft 10A in a slidingly movable manner along the longitudinal direction of the sliding hole 8b for a bearing in a state where the first turning shaft 10A is kept parallel to the second turning shaft 10B held in the circular hole 8a for a bearing by the sliding hole 8b for a bearing.

Moreover, the second coupling member 7 is able to turnably hold the first turning shaft 10A around the centers of the bearing parts 8c and 9c in the state of the first inter-axial distance where the inter-axial distance between the first turning shaft 10A and the second turning shaft 10B is P1, when the shaft part 10a of the first turning shaft 10A has abutted against the bearing parts 8c and 9c in the drivable state.

As illustrated in FIGS. 3 and 4, the driving wire 15 extending along the longitudinal axis O from the proximal side is wound around and engaged with the pulley groove 9a of the driving force input part 9 in the drivable state.

The driving wire 15 is a driving force transmission member that transmits the driving force of the drive motor 25, and in the present embodiment, is wound around the driving pulley 25b of the drive motor 25 and is stretched between the driving force input part 9 and the driving pulley 25b in the drivable state.

In addition, as illustrated in FIG. 5, wire insertion parts 21b that guide the driving wire 15 to the inside of the body part 20 open to the distal end surface 21a of the elongated member 21.

The driving wire 15 engages with the pulley groove 9a of the driving force input part 9 without slipping, and if the driving wire can withstand tension generated when the joint part 3 is driven, the type of the wire is not particularly limited. As an example of a wire suitable as the driving wire 15, for example, the example of a stainless steel wire can be adopted.

Next, wiring of the respective wire members in the joint part 3 will be described.

By adjusting the length of the body part 20 (refer to FIG. 2) when a wire relaxation mechanism 30 (refer to FIG. 2) to be described below is extended and retracted in the longitudinal direction, as illustrated in FIG. 8, in the drivable state, the inter-axial distance between the first turning shaft 10A and the second turning shaft 10B is brought into the state of the first inter-axial distance P1, and the inter-axial distance between the first turning shaft 10A and the driving shaft 25a of the drive motor 25 is L1.

In this state, the driving wire 15 is wound and stretched in an oval shape around the pulley groove 9a provided at the periphery of the driving force input part 9 and a pulley groove 25c provided at the periphery of the driving pulley 25b. In this case, tension is generated in the driving wire 15, and the driving wire 15 is engaged with the pulley grooves 9a and 25c due to frictional force.

Although a case where the driving wire 15 is wound around the pulley groove 25c by a length equivalent to a substantially semi circumference (including a length equivalent to a semi circumference) is illustrated in FIG. 8, the driving wire 15 can also be wound around the pulley groove 25c by one or more circumferences.

In contrast, the driving wire 15 may be wound less than once around the pulley groove 9a, and in the present embodiment, is wound around the pulley groove by a substantially semi circumference (including a semi circumference).

If such wiring is adopted and if the driving pulley 25b turns in the illustrated clockwise direction (or in the counterclockwise direction) as indicated by an illustrated solid line arrow (dashed line arrow), the second coupling member 7 turns in the clockwise direction (or in the counterclockwise direction) around the first turning shaft 10A.

As illustrated in FIG. 9A, the wire 11 for a first guide has the distal end 11a fixed to the wire-fixing parts 5d of the second turning shaft 10B, and is wound in an S-shape around the distal-side pulley 5B and the proximal-side pulley 5A. That is, the wire 11 for a first guide is wired in a circular-arc shape along the pulley groove 5c of the second turning shaft 10B from the wire-fixing part 5d, passes between the pulley groove 5c of the distal-side pulley 5B and the pulley groove 5c of the proximal-side pulley 5A, and is wound around an S-shaped path that is curved in a circular-arc shape along the pulley groove 5c of the proximal-side pulley 5A.

The wire 11 for a first guide extended from the proximal-side pulley 5A extends in a linear shape substantially parallel (including the case of being parallel) to the longitudinal axis O inside the body part 20 (not illustrated), and has the proximal end 11b fixed to a wire-fixing part 14. For this reason, a wire insertion part 21b (refer to FIG. 5) that guides the wire 11 for a first guide to the inside of the body part 20 opens to the distal end surface 21a of the elongated member 21.

The wire-fixing part 14 is fixed to a support 24 of the body part 20 to be described below.

As the configuration of the wire-fixing part 14, all the configurations that can be used for the above-described wire-fixing part 5d can be adopted.

The wire 12 for a second guide has the distal end 12a fixed to a side opposite of the distal end 11a of the wire 11 for a first guide in the wire-fixing part 5d of the second turning shaft 10B, and is wound in an S-shape reversed to the reverse wire 11 for a first guide around the distal-side pulley 5B and the proximal-side pulley 5A. That is, the wire 12 for a second guide is wired in a circular-arc shape along the pulley groove 5c of the second turning shaft 10B from the wire-fixing part 5d, passes between the pulley groove 5c of the distal-side pulley 5B and the pulley groove 5c of the proximal-side pulley 5A, and is wound around an S-shaped path that is curved in a circular-arc shape along the pulley groove 5c of the proximal-side pulley 5A. The wire 12 for a second guide extended from the proximal-side pulley 5A extends in a linear shape substantially parallel (including the case of being parallel) to the longitudinal axis O inside the body part 20 (not illustrated), and has the proximal end 12b fixed to a wire-fixing part 14. For this reason, a wire insertion part 21b (refer to FIG. 5) that guides the wire 12 for a second guide to the inside of the body part 20 opens to the distal end surface 21a of the elongated member 21.

Although the wire-fixing part 14 that fixes the proximal end 11b is different from the wire-fixing part 14 that fixes the proximal end 12b, the wire-fixing parts are the same in their configurations and are also the same in being fixed to the support 24 of the body part 20 to be described below.

By adopting such wiring, the whole circumferences of the pulley grooves 5c of the distal-side pulley 5B are wound by either the wire 11 for a first guide or the wire 12 for a second guide.

Additionally, the pulley grooves 5c of the proximal-side pulley 5A are wound by either the wire 11 for a first guide or the wire 12 for a second guide by less than a total of one round, and in the present embodiment, by substantially a semi circumference (including the case of a semi circumference) as an example.

In this way, the wire 11 for a first guide and the wire 12 for a second guide are wound along the pitch circles of the proximal-side pulley 5A and the distal-side pulley 5B.

For this reason, as illustrated in FIG. 9B, if the plate-shaped part 8 is driven by the drive motor 25 and turns about the first turning shaft 10A, the wire 11 for a first guide and the wire 12 for a second guide move on the respective pulley grooves 5c without slipping. As a result, the distal-side pulley 5B constrained by the wire 11 for a first guide and the wire 12 for a second guide turns about the second turning shaft 10B.

For this reason, the distal-side pulley 5B rolls on the pitch circle of the proximal-side pulley 5A without slipping, with the pitch circle of the distal-side pulley 5B.

Accordingly, for example, as illustrated in FIG. 9B, if the plate-shaped part 8 (not illustrated) turns by an angle θ in the illustrated clockwise direction with respect to the longitudinal axis O, the distal-side pulley 5B turns by the angle θ in the clockwise direction around the second turning shaft 10B. Therefore, the joint part 3 is bent by an angle 2θ with respect to the longitudinal axis O.

Accordingly, the distal-side turning body 4 to which the second turning shaft 10B has been fixed turns similarly.

For example, as illustrated in FIG. 9A, if the treatment part 2 fixed to the distal-side turning body 4 is aligned with the longitudinal axis O before the turning (θ=0°) and the proximal-side pulley 5A turns by the angle θ in the illustrated clockwise direction, the orientation of the treatment part 2 turns by the angle 2θ in the illustrated clockwise direction with respect to the longitudinal axis O, and the orientation of the treatment part 2 is changed.

For this reason, the proximal-side pulley 5A constitutes the first guide part that allows guidance of rolling centered on the first turning shaft 10A.

The distal-side pulley 5B constitutes the second guide part that engages with the proximal-side pulley 5A and guides rolling along the track of the proximal-side pulley 5A.

Next, the configuration of the body part 20 will be described.

As illustrated in FIGS. 2 and 3, the body part 20 includes the elongated member 21, the proximal-side device section 22, and a position-adjusting part 23.

The elongated member 21 has a bottomed cylindrical shape that has the aforementioned distal end surface 21a on the distal side thereof, has a cylindrical inner peripheral surface 21e formed therein, and opens on the proximal side.

As illustrated in FIG. 10A, the proximal end of the elongated member 21 has a proximal end surface 21f orthogonal to the longitudinal axis O formed at an axial end thereof, and has a male screw part 21c for performing positional adjustment with respect to the proximal-side device section 22 provided on an outer peripheral surface thereof.

A guide groove 21d that extends along the longitudinal axis O is provided on the proximal side of the inner peripheral surface 21e of the elongated member 21 in order to restrict the position of the proximal-side device section 22 around the longitudinal axis O with respect to the elongated member 21. In the present embodiment, as illustrated in FIG. 10B, guide grooves 21d are provided at two positions that face each other with the longitudinal axis O interposed therebetween.

The proximal-side device section 22 includes the drive motor 25 and the support 24.

The support 24 includes a housing part 24f that fixes the above-described drive motor 25 (not illustrated in FIGS. 10A and 10B, refer to FIGS. 2 and 3), and a tubular part 24a that is fitted to the inner peripheral surface 21e of the elongated member 21. The housing part 24f and the tubular part 24a are provided on the proximal side of the support 24.

An inner peripheral surface 24e of the tubular part 24a is formed with a size such that the driving wire 15 can be inserted through the tubular part without contact, and the respective wire-fixing parts 14 (not illustrated in FIGS. 10A and 10B, refer to FIGS. 3 and 9) are fixed to the inner peripheral surface 24e of the tubular part 24a. An outer peripheral surface 24b of the tubular part 24a consists of a cylindrical surface that is movably fitted to the inner peripheral surface 21e of the elongated member 21 in a direction along the longitudinal axis O.

A pair of engaging projections 24d that respectively engage with the pair of guide grooves 21d of the elongated member 21 protrude radially outward on the distal side of the outer peripheral surface 24b.

Engaging projections 24c that engage with a guide groove 23d of the position-adjusting part 23 to be described below protrude radially outward on the proximal side of the outer peripheral surface 24b.

By virtue of such a configuration, the elongated member 21 of the body part 20 constitutes an elongated part that has the longitudinal axis O and is connected to the end of the joint part 3 opposite to a side where the treatment part 2 that is an end effector is arranged. Additionally, the proximal-side device section 22 constitutes a driving part that is provided on the proximal side of the elongated part and supplies a driving force for operating the second coupling member 7 that is a rotating body.

As illustrated in FIGS. 10A and 10B, the position-adjusting part 23 is a member that adjusts the relative positions of the elongated part and the driving part in the direction along the longitudinal axis O, and consists of a tubular member that threadably engages with the male screw part 21c of the elongated member 21 and is externally fitted to the tubular part 24a of the support 24. The position-adjusting part 23 is arranged between the elongated member 21 and the proximal-side device section 22.

A female screw part 23c that threadably engages with the male screw part 21c is provided at an inner peripheral part on the distal side of the position-adjusting part 23. An inner peripheral surface 23b that is slidably fitted to the outer peripheral surface 24b of the tubular part 24a, and the guide groove 23d that extends over the whole circumference of the inner peripheral surface 23b are formed at a proximal end of the inner peripheral part of the position-adjusting part 23. Additionally, the guide groove 23d engages with the engaging projections 24c of the tubular part 24a in an intermediate part of the inner peripheral surface 23b.

By virtue of such a configuration, the position-adjusting part 23 is provided so as to be rotatable in the circumferential direction of the tubular part 24a in a state where the position thereof in the direction along the longitudinal axis O with respect to the tubular part 24a is constant.

Meanwhile, the male screw part 21c of the elongated member 21 is threadably engaged with the female screw part 23c of the position-adjusting part 23. Therefore, if the position-adjusting part 23 is rotated with respect to the tubular part 24a of the support 24, the elongated member 21 changes only its relative position with respect with the support 24 in the direction along the longitudinal axis O without relatively rotating with respect to the support 24.

That is, the proximal end surface 21f of the elongated member 21 moves in the direction along the longitudinal axis O with the rotation of the position-adjusting part 23.

The position-adjusting part 23 has a stopper part 29 that performs the fixation and release of the position of the proximal end surface 21f that moves in this way, thereby restricting the relative movement between the elongated member 21 and the proximal-side device section 22.

The stopper part 29 is configured to include a stopper member 26 and a coil spring 27 (elastic member), in a stopper member-housing hole 23a formed at a side of the position-adjusting part 23.

Stopper member-housing holes 23a are provided at two positions that face each other with a central axis therebetween in the circumferential direction of the position-adjusting part 23.

The hole shape of each stopper member-housing hole 23a in a side view is a rectangular shape that is long in the direction along the longitudinal axis O (refer to FIG. 3).

The hole shape of each stopper member-housing hole 23a in the radial direction has a depth such that the distal side of the stopper member-housing hole passes through the female screw part 23c and the proximal side thereof is located closer to a radial outer side than the guide groove 23d. A proximal end bottom surface 23f is formed in the stopper member-housing hole 23a.

A distal end inner peripheral surface 23e of the stopper member-housing hole 23a is located closer to the proximal side than the engaging projection 24d of the tubular part 24a.

A turning supporting shaft 28 that turnably supports the stopper member 26 in the lateral direction is provided at a central part of the stopper member-housing hole 23a in the longitudinal direction.

The stopper member 26 is a plate-shaped member that has a rectangular outer shape capable of being inserted into the stopper member-housing hole 23a and that is turnably supported by the turning supporting shaft 28 of the stopper member-housing hole 23a.

The stopper member 26 is bent in a shape that becomes convex toward the inside of the position-adjusting part 23 at a substantially central part in the longitudinal direction. The turning supporting shaft 28 is inserted through a curved part of the stopper member 26 in the lateral direction.

The stopper member 26 closer to the distal side than the turning supporting shaft 28 extends in a plate shape toward the distal end inner peripheral surface 23e, and a locking end surface 26b that locks the proximal end surface 21f of the elongated member 21 is formed on the distal side of the stopper member 26.

The locking end surface 26b of the stopper member 26 is located radially inside a thread ridge portion of the female screw part 23c as illustrated in FIG. 10A with the turning of the stopper member 26 around the turning supporting shaft 28, and is movable between a position where the proximal end surface 21f of the elongated member 21 that moves along the longitudinal axis O is lockable, and a position (refer to FIG. 11) that faces the distal end inner peripheral surface 23e radially outside the thread ridge portion of the female screw part 23c.

The part of the stopper member 26 closer to the proximal side than the turning supporting shaft 28 is bent in a shape that becomes convex toward the outside of the position-adjusting part 23 in an intermediate part between the turning supporting shaft 28 and the distal end on the proximal side, and a plate-shaped pressing part 26a (manipulation part) is formed on the proximal side of the curved part.

The pressing part 26a protrudes further radially outward than the outer peripheral surface of the position-adjusting part 23 as illustrated in FIG. 10A with the turning of the stopper member 26 around the turning supporting shaft 28, and is movable between a position where the pressing part can be pressed toward the radial inner side in the stopper member-housing hole 23a from the radial outer side, and a position (refer to FIG. 11) where the pressing part is hidden in the inside of the stopper member-housing hole 23a.

The coil spring 27 is an elastic member that biases the stopper member 26 in a direction in which the locking end surface 26b of the stopper member 26 advances to a movement path of the elongated member 21, and is arranged between a back surface of the pressing part 26a and the proximal end bottom surface 23f of the position-adjusting part 23.

The male screw part 21c of the elongated member 21, the position-adjusting part 23, and the stopper member 26 constitute the wire relaxation mechanism 30.

Such a wire relaxation mechanism 30 is arranged at the proximal end of the elongated member 21, and encapsulates the driving wire 15.

The wire relaxation mechanism 30 is a mechanism that is extended and retracted in the longitudinal direction of the elongated member 21 as is clear from the description of operation to be described below, thereby changing the path length of the driving wire 15 between the second coupling member 7 that is a rotating body and the proximal-side device section 22 that is a driving part.

Next, a switching operation between the drivable state and the relaxation state about the operation of the medical manipulator 1 having such a configuration will mainly be described.

Figure 11:
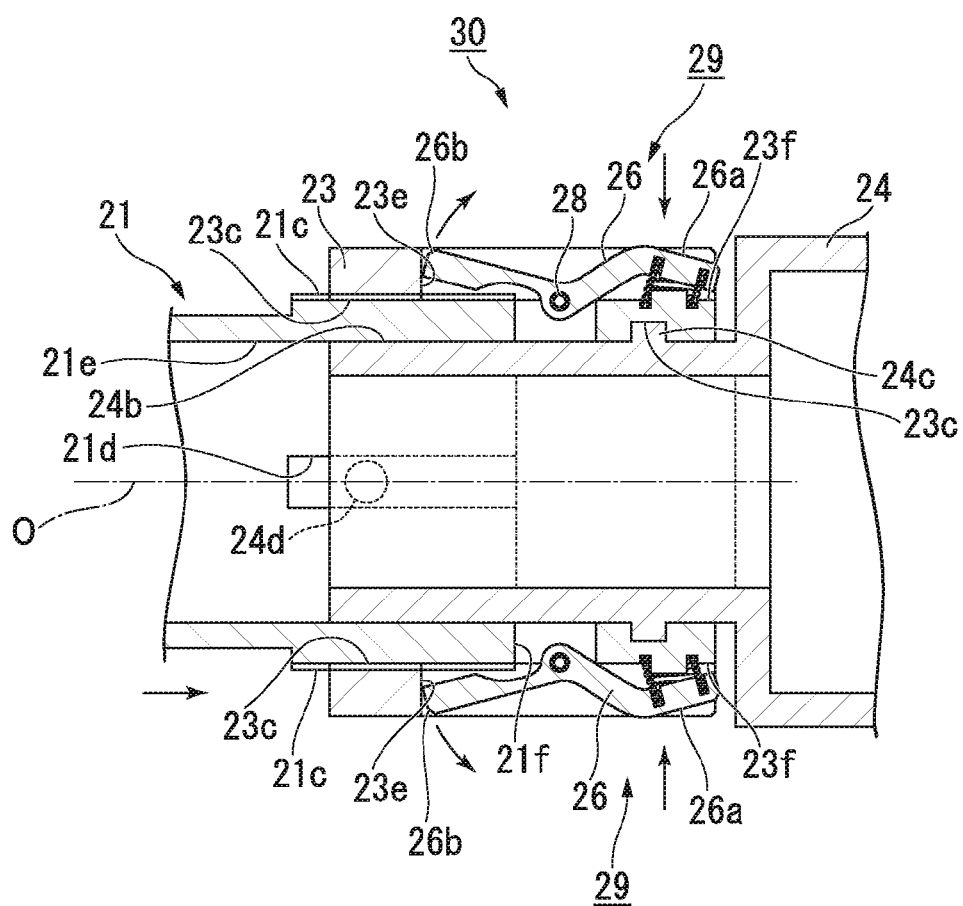
FIG. 11 is an operation explanatory view of a stopper part of the medical manipulator of the first embodiment of the invention.
Figure 12A:
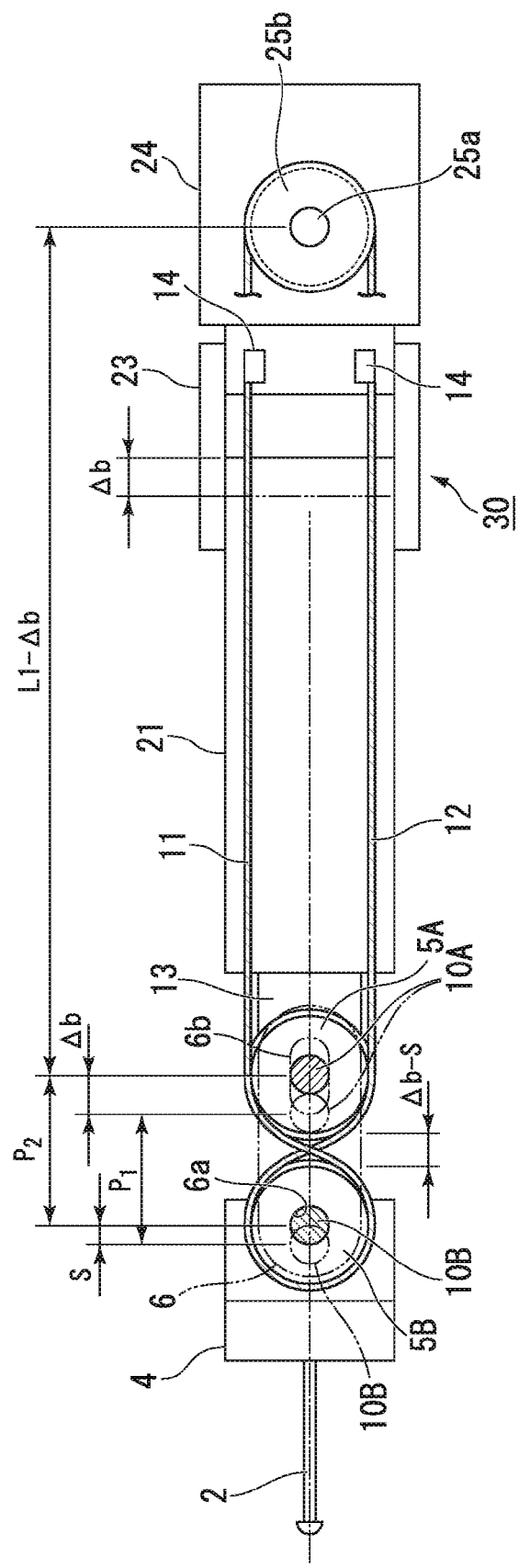
FIG. 12A is an operation explanatory view of the medical manipulator of the first embodiment of the invention.
Figure 12B:
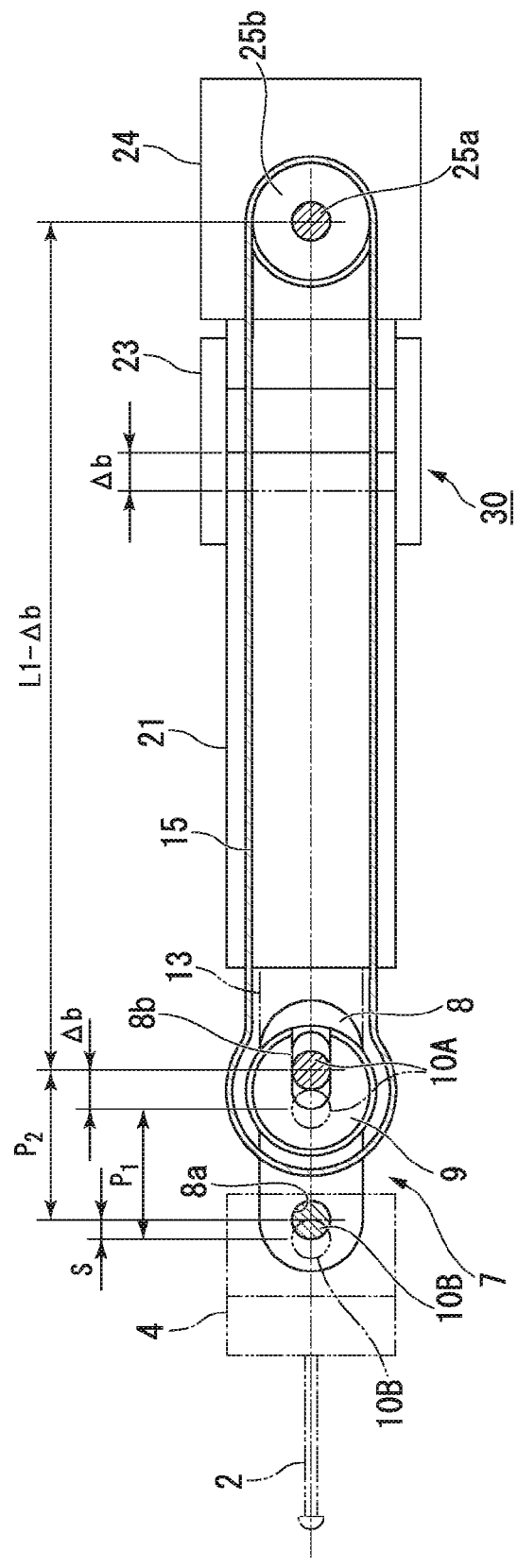
FIG. 12B is an operation explanatory view of the medical manipulator of the first embodiment of the invention.

FIG. 11 is an operation explanatory view of the stopper part of the medical manipulator of the first embodiment of the invention. FIGS. 12A and 12B are operation explanatory views of the medical manipulator of the first embodiment of the invention.

In order to perform a treatment using the medical manipulator 1, the medical manipulator 1 is assembled in the drivable state, and is mounted on the slave manipulator 120 as illustrated in FIG. 1.

In this case, as illustrated in FIG. 2, in the medical manipulator 1, the axis of the treatment part 2 and the central axes of the second turning shaft 10B and the first turning shaft 10A are aligned with each other on the longitudinal axis O, and the inter-axial distance between the second turning shaft 10B and the first turning shaft 10A is the first inter-axial distance P1. Additionally, the inter-axial distance between the first turning shaft 10A and the driving shaft 25a is L1.

The inter-axial distance L1 is realized by adjusting the distance in the direction along the longitudinal axis O between the elongated member 21 and the support 24, using the position-adjusting part 23. In the present embodiment, as illustrated in FIG. 10A, the center distance is realized when the proximal end surface 21f of the elongated member 21 is aligned with the distal end inner peripheral surface 23e of the stopper member-housing hole 23a.

In the medical manipulator 1, the locking end surface 26b of the stopper member 26 of the stopper part 29 is locked to the proximal end surface 21f and the distal end inner peripheral surface 23e in the state of such an inter-axial distance L1. For this reason, even if an attempt to turn the position-adjusting part 23 around the longitudinal axis O to move the elongated member 21 to the support 24 side is made, the movement is prevented by the stopper member 26 and is in a locked state.

Additionally, since the locking end surface 26b of the stopper member 26 is biased in a radially inward direction by the coil spring 27, this locked state is maintained until this biasing is released. In this case, the pressing part 26a of the stopper member 26 protrudes to the outside of the position-adjusting part 23.

If the treatment is completed, it is necessary to clean the medical manipulator 1. The medical manipulator 1 can be easily cleaned by bringing the joint part 3 into the relaxation state at the time of cleaning.

In order to shift from the drivable state to the relaxation state, the relative distance between the elongated member 21 and the support 24 is shortened by the position-adjusting part 23.

First, as illustrated in FIG. 11, a cleaning staff presses each pressing part 26a in the stopper part 29 against the inside of the position-adjusting part 23. As a result, the coil spring 27 is compressed, the biasing force is released, and each stopper member 26 turns around the turning supporting shaft 28.

As a result, each locking end surface 26b moves to the radial outer side that faces the distal end inner peripheral surface 23e in the stopper member-housing hole 23a, and the locking of the proximal end surface 21f of the elongated member 21 by the locking end surface 26b is released. In this way, a space where the elongated member 21 is movable is formed closer to the proximal side than the proximal end surface 21f when the stopper member 26 is withdrawn from the movement path of the elongated member 21.

The cleaning staff presses the pressing part 26a, turns the position-adjusting part 23 around the longitudinal axis O in the pressed state, and twists the position-adjusting part 23. Accordingly, the elongated member 21 and the tubular part 24a are engaged with each other in the circumferential direction by the guide grooves 21d, and the engaging projections 24d. The elongated member 21 moves in a direction approaching or in a direction separating from the support 24, according to the turning direction of position-adjusting part 23.

In order to bring about the relaxation state, the elongated member 21 is made to approach the support 24 by twisting the position-adjusting part 23 to shorten the wire relaxation mechanism 30, and the distance between the wire-fixing part 14 and the first turning shaft 10A and the inter-axial distance between the driving shaft 25a and the first turning shaft 10A are shortened.

For example, as illustrated in FIGS. 12A and 12B, the elongated member 21 is brought close to the support 24 by a distance Δb.

In this case, the proximal-side support 13 of the joint part 3 coupled to the elongated member 21 also moves in parallel to the proximal side by the distance Δb together with the first turning shaft 10A, and for example, the inter-axial distance between the first turning shaft 10A and the driving shaft 25a reaches L1−Δb.

Since the first turning shaft 10A is supported in a slidingly movable manner by the sliding hole 8b for a bearing in the sliding hole 6b for a bearing of the first coupling member 6, and the second coupling member 7, the distal-side turning body 4 can maintain the same position as in the drivable state. For this reason, the state of a second inter-axial distance where the inter-axial distance of the first turning shaft 10A and the second turning shaft 10B is greater than the first inter-axial distance is possible.

In this state, as illustrated in FIG. 12B, the driving wire 15 stretched between the driving force input part 9 and the driving shaft 25a is relaxed, and the engagement with the driving force input part 9 is released.

Meanwhile, since the wire 11 for a first guide and the wire 12 for a second guide are stretched between the distal-side pulley 5B and the support 24, only the engagement with the proximal-side pulley 5A supported by the first turning shaft 10A is released, and the wire 11 for a first guide and the wire 12 for a second guide, and the distal-side pulley 5B are still engaged with each other.

Thus, the distal-side turning body 4 is moved to the elongated member 21 side (refer to FIG. 12A) by a distance S (where 0<S<Δb). If the distal-side turning body 4 is moved by the distance S, the first coupling member 6 and the second coupling member 7 that hold the second turning shaft 10B also move in parallel by the distance S.

In addition, since the first turning shaft 10A is held in a relatively slidingly movable manner by the sliding holes 6b and 8b for a bearing, even if the first coupling member 6 and the second coupling member 7 move by the distance S, the positions of the first turning shaft 10A and the proximal-side support 13 do not change. In this way, the inter-axial distance between the first turning shaft 10A and the second turning shaft 10B reaches P2=P1+S, and reaches the second inter-axial distance greater than the first inter-axial distance P1 by the distance S.

Accordingly, the proximal-side pulley 5A and the distal-side pulley 5B are spaced apart from each other by a distance Δb−S, and the wire 11 for a first guide and the wire 12 for a second guide are brought into a relaxed state on the outer peripheral sides of the distal-side pulley 5B and the proximal-side pulley 5A.

In this way, the engagement between the proximal-side pulley 5A and the distal-side pulley 5B, and the wire 11 for a first guide and the wire 12 for a second guide is released.

In this way, in the relaxation state, the driving wire 15, the wire 11 for a first guide, and the wire 12 for a second guide are all relaxed in the joint part 3, the engagement between the driving wire 15 and the driving force input part 9, the engagement between the wire 11 for a first guide and the proximal-side pulley 5A, and the engagement between the wire 12 for a second guide and the distal-side pulley 5B are released, and a gap is also formed inside the joint part 3. For this reason, for example, the cleaning work of inserting a brush becomes simple. Additionally, in the joint part 3, a cleaning agent reliably runs on the surfaces of the respective members, there is no cleaning leakage, and cleaning can be rapidly and reliably performed.

After the cleaning, the inter-axial distance is increased from the relaxation state by twisting the position-adjusting part 23 to extend the wire relaxation mechanism 30. Accordingly, the wires can be stretched again and tensioned and returned to their original drivable state, and the medical manipulator 1 can be brought into a reusable state. That is, it is not necessary to return the medical manipulator to the manufacturer, and the cleaning staff can clean the medical manipulator 1 in the hospital to return the medical manipulator 1 to a drivable state.

First Modification Example

Next, a medical manipulator of a first modification example of the present embodiment will be described.

Figure 13:
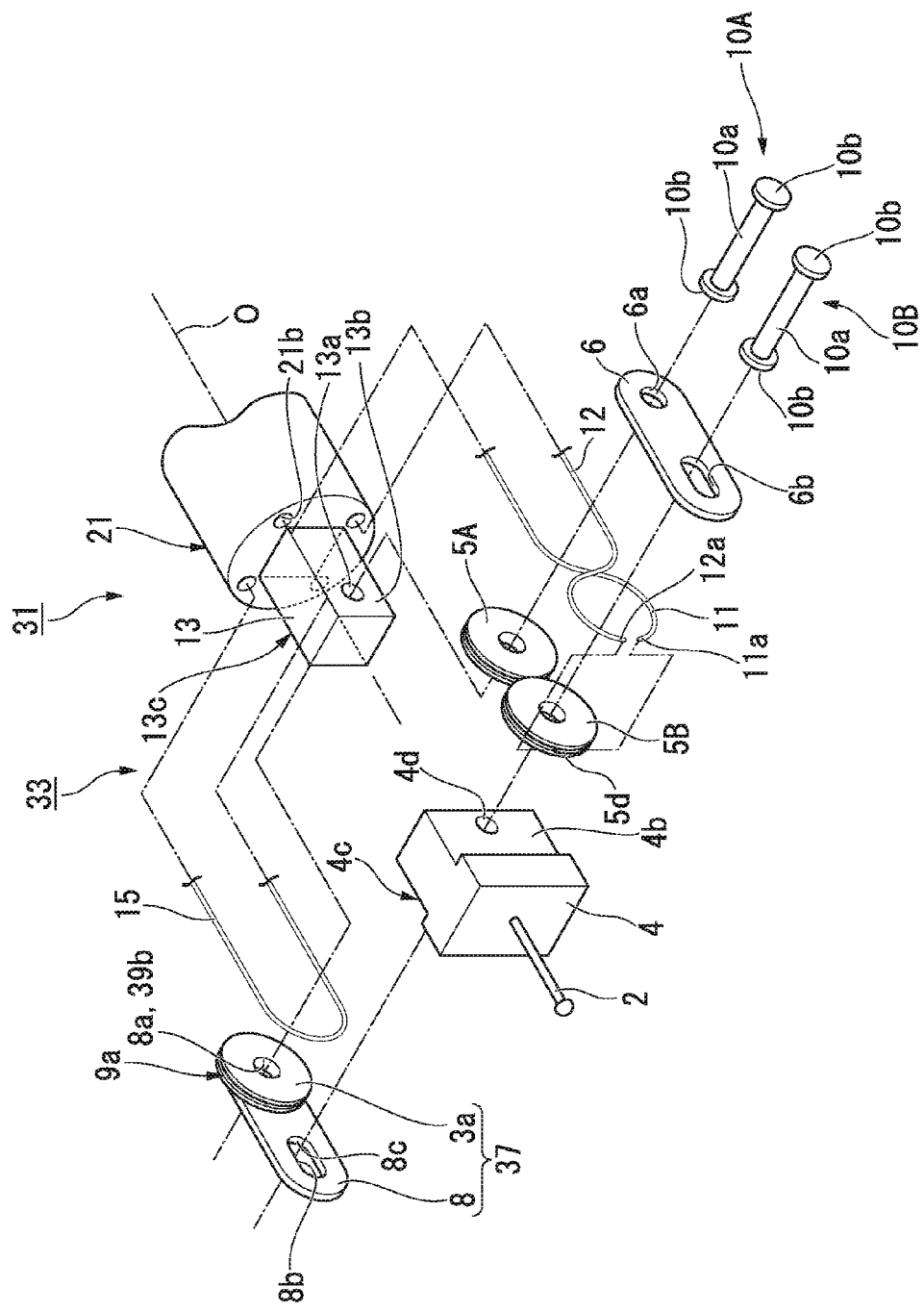
FIG. 13 is a schematic exploded perspective view of a joint part of a medical manipulator of a first modification example of the first embodiment of the invention.

FIG. 13 is a schematic exploded perspective view of a joint part of the medical manipulator of the first modification example of the first embodiment of the invention.

As illustrated in FIG. 13, a medical manipulator 31 of the present modification example includes a joint part 33 instead of the joint part 3 of the medical manipulator 1 of the aforementioned first embodiment.

As illustrated in FIG. 1, the medical manipulator 31 can be used as a portion of the medical system 100 instead of the medical manipulator 1 of the aforementioned first embodiment.

Hereinafter, differences from the aforementioned first embodiment will mainly be described.

As illustrated in FIG. 13, the joint part 33 includes a second coupling member 37 (a rotating body, a coupling member) instead of the second coupling member 7 of the joint part 3 in the aforementioned first embodiment, and the attachment position of the first coupling member 6 is changed.

The second coupling member 37 includes a driving force input part 39 instead of the driving force input part 9 of the second coupling member 7 in the aforementioned first embodiment.

The driving force input part 39 is a pulley part obtained by eliminating the U-shaped groove 9b for a bearing of the driving force input part 9 and forming the pulley groove 9a on the whole circumference, and accordingly, includes a circular hole 39b for a bearing having the same circular diameter as the circular hole 8a for a bearing, instead of the bearing part 9c.

The driving force input part 39 is fixed to or molded integrally with one surface of the plate-shaped part 8 so that the circular hole 39b for a bearing is located on the coaxial position as the circular hole 8a for a bearing.

The second coupling member 37 having such a configuration is arranged so that the driving force input part 39 faces the second side surface 13c of the proximal-side support 13 and is retained in the axial direction by the retaining parts 10b of the first turning shaft 10A in a state where the shaft part 10a of the first turning shaft 10A has been inserted through the circular holes 8a and 39b for a bearing.

Additionally, the plate-shaped part 8 is arranged parallel to the second side surface 4c of the distal-side turning body 4 and is retained in the axial direction by the retaining parts 10b of the second turning shaft 10B, in a state where the shaft part 10a of the second turning shaft 10B has been inserted through the sliding hole 8b for a bearing.

Accordingly, the second coupling member 37 turnably holds the first turning shaft 10A around the center of the circular hole 8a for a bearing, using the circular holes 8a and 39b for a bearing.

Additionally, the second coupling member 37 holds the second turning shaft 10B in a slidingly movable manner along the longitudinal direction of the sliding hole 8b for a bearing in a state where the second turning shaft 10B is kept parallel to the first turning shaft 10A held in the circular hole 8a for a bearing by the sliding hole 8b for a bearing.

Moreover, the second coupling member 7 is able to turnably hold the second turning shaft 10B around the center of the bearing part 8c in the state of the first inter-axial distance where the inter-axial distance between the second turning shaft 10B and the first turning shaft 10A is P1, when the shaft part 10a of the second turning shaft 10B has abutted against the bearing part 8c in the drivable state.

The driving wire 15 being wound around the pulley groove 9a of the driving force input part 39 is the same as that of the aforementioned first embodiment instead of the driving force input part 9 of the aforementioned first embodiment.

The first coupling member 6 in the joint part 33 is made to correspond to the aforementioned configuration of the second coupling member 37, and is arranged by replacing the circular hole 6a for a bearing and the sliding hole 6b for a bearing of the aforementioned first embodiment.

That is, the shaft part 10a of the first turning shaft 10A is inserted through the circular hole 6a for a bearing of the first coupling member 6 and the through-hole 5b of the proximal-side pulley 5A. The proximal side of the first coupling member 6 is retained in the axial direction by the retaining parts 10b of the first turning shaft 10A.

Additionally, the shaft part 10a of the second turning shaft 10B is inserted through the sliding hole 6b for a bearing of the first coupling member 6 and the through-hole 5b of the distal-side pulley 5B. The distal side of the first coupling member 6 is retained in the axial direction by the retaining parts 10b of the second turning shaft 10B.

Accordingly, the first coupling member 6 of the present modification example turnably holds the first turning shaft 10A around the center of the circular hole 6a for a bearing, using the circular hole 6a for a bearing.

Additionally, the first coupling member 6 of the present modification example holds the second turning shaft 10B in a slidingly movable manner along the longitudinal direction of the sliding hole 6b for a bearing in a state where the second turning shaft 10B is kept parallel to the first turning shaft 10A held in the circular hole 6a for a bearing by the sliding hole 6b for a bearing.

Moreover, the first coupling member 6 is able to turnably hold the second turning shaft 10B around the center of the bearing part 6c in the state of the first inter-axial distance where the inter-axial distance between the first turning shaft 10A and the second turning shaft 10B is P1, when the shaft part 10a of the second turning shaft 10B has abutted against the bearing part 6c in the drivable state.

According to the medical manipulator 31 having the joint part 33 having such a configuration, there is a difference only in that the first coupling member 6 and the second coupling member 37 move together with the proximal-side support 13 with the movement of the elongated member 21 at the time of relaxation, and the drivable state and the relaxation state can be switched therebetween, similar to the medical manipulator 1 of the aforementioned first embodiment.

For this reason, the medical manipulator having the joint part can be more efficiently and more easily cleaned, similar to the aforementioned first embodiment.

Second Embodiment

Next, a medical manipulator of a second embodiment of the invention will be described.

Figure 14A:
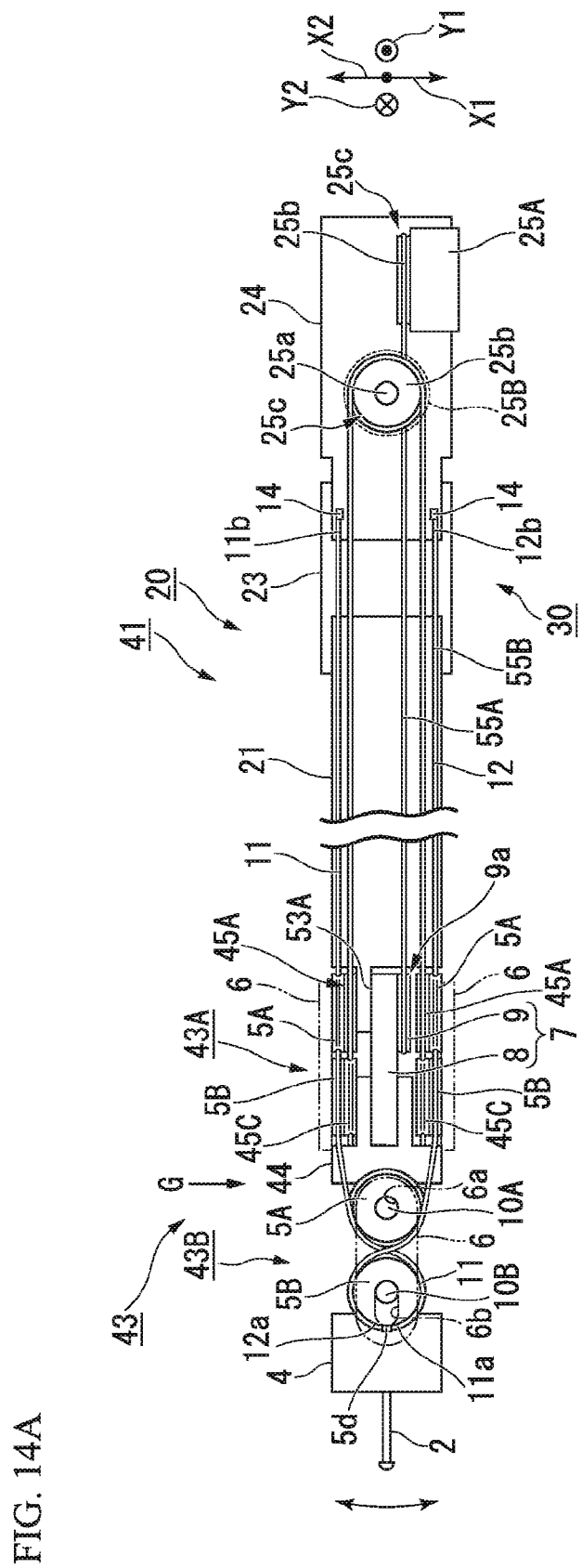
FIG. 14A is a schematic view illustrating the configuration of a medical manipulator of a second embodiment of the invention.
Figure 14B:
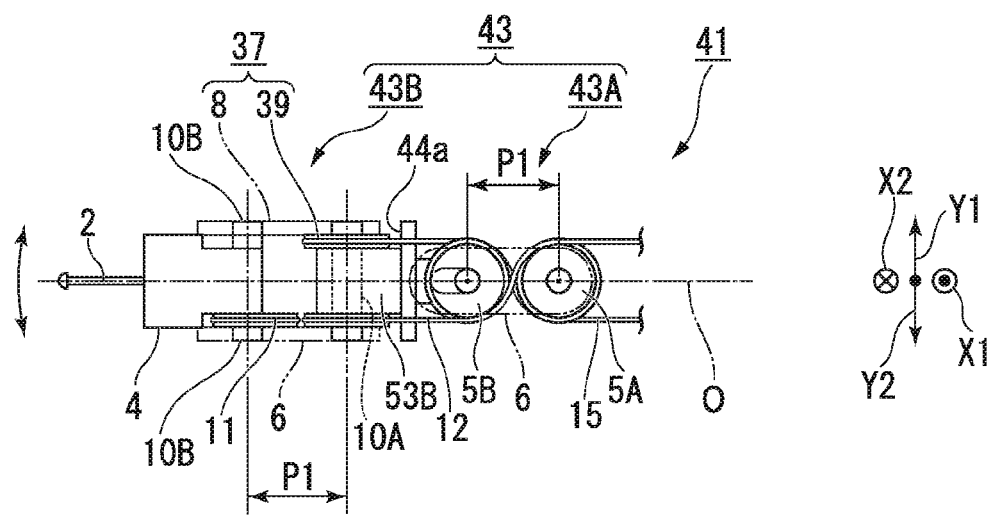
FIG. 14B is a view as seen from G of FIG. 14A.
Figure 15:
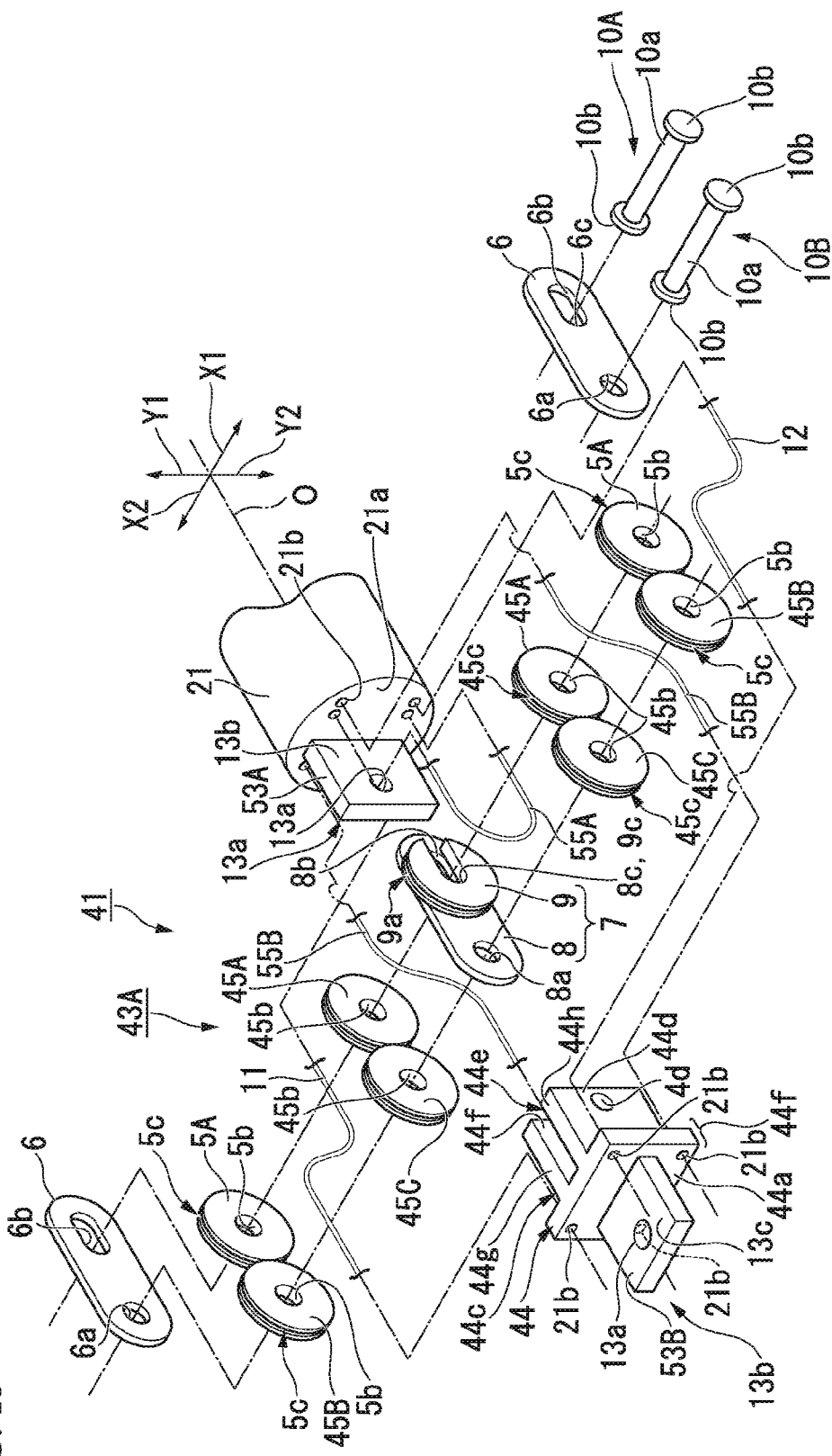
FIG. 15 is a schematic exploded perspective view illustrating wiring of a driving wire member and a guide wire of the medical manipulator of the second embodiment of the invention.

FIG. 14A is a schematic view illustrating the configuration of the medical manipulator of the second embodiment of the invention. FIG. 14B is a view as viewed from G in FIG. 14A. FIG. 15 is a schematic exploded perspective view illustrating wiring of a driving wire member and a guide wire of the medical manipulator of the second embodiment of the invention.

As illustrated in FIGS. 14A and 14B, a medical manipulator 41 of the present embodiment includes a joint part 43 constituted of a first joint 43A (first unit joint) and a second joint 43B (second unit joint) instead of the joint part 3 of the medical manipulator 1 of the aforementioned first embodiment. Additionally, the medical manipulator 41 includes drive motors 25A and 25B having the same configuration as the drive motor 25, and driving wires 55A and 55B (driving wire members), instead of the drive motor 25 and the driving wire 15 of the aforementioned first embodiment.

The drive motor 25A is a driving source that drives the first joint 43A via the driving wire 55A, and the drive motor 25B is a driving source that drives the second joint 43B via the driving wire 55B.

That is, the medical manipulator 41 is an example in which the joint part is formed by coupling the two unit joints in series.

As illustrated in FIG. 1, the medical manipulator 41 can be used as a portion of the medical system 100 instead of the medical manipulator 1 of the aforementioned first embodiment.

Hereinafter, differences from those of the aforementioned first embodiment and the aforementioned first modification example will mainly be described.

In addition, in the medical manipulator 41, the joint part 43 is bendable in biaxial directions, and the length thereof in the direction along the longitudinal axis O of the body part 20 is changeable by the position-adjusting part 23, similar to the aforementioned first embodiment. Thus, also in the present embodiment, similar to the aforementioned first embodiment, a state where the driving of the joint part 43 is possible is referred to as the drivable state, and a state where the engagement between members used for driving in the joint part 43 is released and the driving is impossible is referred to as the relaxation state. In the following description, unless particularly mentioned in describing the positional relationship of the respective members in the drivable state, as illustrated in FIGS. 14A and 14B, description will be made on the basis of a state where the joint part 43 does not turn with respect to the longitudinal axis O.

As illustrated in FIG. 15, the first joint 43A is a unit joint that turnably couples the elongated member 21 and the second joint 43B in directions (Illustrated Y1 direction and Y2 direction) intersecting the longitudinal axis O, and includes a proximal-side support 53 and a distal-side turning body 44 instead of the proximal-side support 13 and the distal-side turning body 4 of the aforementioned first embodiment. Additionally the first coupling member (coupling member) 6 and the proximal-side pulley 5A are increased to two sets, the distal-side pulley 5B is not included, and two sets of distal-side pulleys (second pulleys) 45B, a proximal idler pulley (first pulley) 45A, and a distal-side idler pulley (second pulley) 45C are added.

The proximal-side support 53A includes the first side surface 13b, the second side surface 13c, and the turning shaft-holding part 13a, similar to the proximal-side support 13 of the aforementioned first embodiment, and is the same member as the aforementioned first embodiment except that the plate thickness between the first side surface 13b and the second side surface 13c and the fixation positions thereof with respect to the distal end surface 21a.

The normal lines of the first side surface 13b and the second side surface 13c are directed to directions (illustrated X1 direction and X2 direction) orthogonal to the illustrated Y1 and Y2 directions. The first side surface 13b is a side surface in the illustrated X1 direction in the proximal-side support 53A, and the second side surface 13c is a side surface in the illustrated X2 direction in the proximal-side support 53A.

The distal-side turning body 44 has a proximal-side support 53B of the second joint 43B to be described below fixed to the distal side thereof, and includes a rectangular first plate-shaped part 44f in which a distal end surface 44a consisting of a planar surface orthogonal to the longitudinal axis O is formed, and a second plate-shaped part 44g and a third plate-shaped part 44h that are erected from the back side of the distal end surface 44a in the first plate-shaped part 44f The second plate-shaped part 44g is located near the illustrated X2 direction, and the third plate-shaped part 44h is located near the illustrated X1 direction.

The second plate-shaped part 44g has a first side surface 44b that is aligned with the first side surface 13b of the proximal-side support 13A, and a second side surface 44c that is aligned with the second side surface 13c.

The third plate-shaped part 44h has a first side surface 44d and a second side surface 44e, and the plate thickness therebetween is a thickness equal to greater than the thickness of the driving force input part 9 of the second coupling member 7.

The second side surface 44e is arranged with a gap into which the plate-shaped part 8 of the second coupling member 7 is insertable, at a position that faces the first side surface 44b of the second plate-shaped part 44g.

The third plate-shaped part 44h is provided with a turning shaft-holding part 4d, similar to the aforementioned first embodiment. Accordingly, the second turning shaft 10B can be fixed to both of the first side surface 44d and the second side surface 44e, respectively, by the turning shaft-holding part 4d.

Additionally, although illustration is omitted, a circular hole through which the shaft part 10a of the second turning shaft 10B is insertable is provided at a position that faces the turning shaft-holding part 4d, in the second plate-shaped part 44g.

The distal-side pulley 45B has a configuration that does not include the wire-fixing parts 5d of the distal-side pulley 5B of the aforementioned first embodiment.

The proximal idler pulley 45A is turnably supported by the shaft part 10a of the first turning shaft 10A of the first joint 43A, and has the driving wire 55B wound therearound and inserted through the first joint 43A. The proximal idler pulley 45A has pulley grooves 45c having a smaller pitch diameter than P1, and a shaft hole 45b that is turnably fitted to the shaft part 10a of the first turning shaft 10A and is formed coaxially with the pitch circle. The external diameter of the proximal idler pulley 45A is smaller than the external diameter of the proximal-side pulley 5A.

The distal-side idler pulley 45C includes the same pulley grooves 45c and shaft hole 45b as those of the proximal idler pulley 45A.

However, the shaft part 10a of the second turning shaft 10B is inserted through the shaft hole 45b of the distal-side idler pulley 45C, and has a smaller external diameter than the external diameter of the distal-side pulley 5B.

Here, the positional relationship of the respective members of the first joint 43A will be described.

The second coupling member 7 is arranged on the first side surface 13b of the proximal-side support 53A so as to face the proximal side of the plate-shaped part 8 having the sliding hole 8b for a bearing, and the proximal idler pulley 45A and the proximal-side pulley 5A are sandwiched between the driving force input part 9 of the second coupling member 7, and the proximal side (a side having the sliding hole 6b for a bearing) of the first coupling member 6.

The shaft part 10a of the first turning shaft 10A is inserted through the sliding hole 8b for a bearing of the second coupling member 7, the shaft hole 45b of the proximal idler pulley 45A, the through-hole 5b of the proximal-side pulley 5A, and the sliding hole 6b for a bearing of the first coupling member 6. The proximal side of the first coupling member 6 is retained in the axial direction by the retaining parts 10b of the first turning shaft 10A. The proximal idler pulley 45A and the proximal-side pulley 5A are arranged in this order on the second side surface 13c of the proximal-side support 53A, and are sandwiched between the second side surface and the proximal side (a side having the sliding hole 6b for a bearing) of the first coupling member 6.

The shaft part 10a of the first turning shaft 10A is inserted through the shaft hole 45b of the proximal idler pulley 45A, the through-hole 5b of the proximal-side pulley 5A, and the sliding hole 6b for a bearing of the first coupling member 6. The proximal side of the first coupling member 6 is retained in the axial direction by the retaining parts 10b of the other first turning shaft 10A.

The distal end of the plate-shaped part 8 is inserted between the second plate-shaped part 44g and the third plate-shaped part 44h of the distal-side turning body 44.

The distal-side idler pulley 45C and the distal-side pulley 45B are arranged in this order on the first side surface 44d of the third plate-shaped part 44h, and are sandwiched between the first side surface 44d and the distal side (a side having the circular hole 6a for a bearing) of the first coupling member 6.

The shaft part 10a of the second turning shaft 10B is inserted through the shaft hole 45b of the distal-side idler pulley 45C, the through-hole 5b of the distal-side pulley 45B, and the circular hole 6a for a bearing of the first coupling member 6. The distal side of the one first coupling member 6 is retained in the axial direction by the retaining parts 10b of the second turning shaft 10B.

The distal-side idler pulley 45C and the distal-side pulley 45B are arranged in this order on the second side surface 44c of the second plate-shaped part 44g, and are sandwiched between the second side surface 44c and the distal side (a side having the circular hole 6a for a bearing) of the first coupling member 6.

The shaft part 10a of the first turning shaft 10A is inserted through the circular hole 8a for a bearing of the plate-shaped part 8, and the circular hole (not illustrated) of the second plate-shaped part 44g, the shaft hole 45b of the distal-side idler pulley 45C, the through-hole 5b of the proximal-side pulley 5A, and the sliding hole 6b for a bearing of the first coupling member 6. The proximal side of the first coupling member 6 is retained in the axial direction by the retaining parts 10b of the first turning shaft 10A.

By virtue of such a configuration, each first coupling member 6 of the first joint 43A turnably holds each second turning shaft 10B around the center of the circular hole 6a for a bearing, using each circular hole 6a for a bearing.

Additionally, each first coupling member 6 holds each first turning shaft 10A in a slidingly movable manner along the longitudinal direction of each sliding hole 6b for a bearing in a state where each first turning shaft 10A is kept parallel to each second turning shaft 10B held in each circular hole 6a for a bearing by each sliding hole 6b for a bearing.

Moreover, each first coupling member 6 is able to rotatably hold each first turning shaft 10A around the center of the bearing part 6c in the state of the first inter-axial distance where the inter-axial distance between the first turning shaft 10A and the second turning shaft 10B is P1, when the shaft part 10a of each first turning shaft 10A has abutted against each bearing part 6c in the drivable state.

Next, wiring of the respective wire members in the first joint 43A will be described.

As illustrated in FIG. 14A, the driving wire 55A is wound and stretched in the same oval shape as that of the driving wire 15 of the aforementioned first embodiment around the pulley groove 9a of the driving force input part 9 and the pulley groove 25c of the driving pulley 25b of the drive motor 25A. In this case, a frictional force is generated in the driving wire 55A, and the driving wire 55A is engaged with the pulley grooves 9a and 25c due to the frictional force.

If such wiring is adopted and if the driving pulley 25b of the drive motor 25A turns, the second coupling member 7 of the first joint 43A turns in the same direction around the first turning shaft 10A.

As illustrated in FIGS. 14A and 14B, the driving wire 55B is stretched over the pulley groove 9a of the second coupling member 37 in the second joint 43B to be described below and the pulley groove 25c of the driving pulley 25b of the drive motor 25B.

For this reason, as illustrated in FIG. 15, the driving wires 55B are inserted as two driving wire members between the wire insertion parts 21b provided in the distal end surface 21a of the elongated member 21 and the wire insertion parts 21b of the first plate-shaped part 44f of the distal-side turning body 44 within the first joint 43A.

The driving wires 55B are all engaged with the respective pulley grooves 45c of the proximal idler pulley 45A and the distal-side idler pulley 45C, which face each other in the radial direction, in an S-shape.

In the wire 11 for a first guide, and the wire 12 for a second guide, as illustrated in FIG. 14A, similar to the aforementioned first embodiment, the proximal ends 11b and 12b are fixed to the wire-fixing parts 14 via the wire-fixing parts 14, and the distal ends 11a and 12a are respectively fixed to the wire-fixing parts 5d of the two distal-side pulleys 5B in the second joint 43B to be described below and are stretched between the respective distal-side pulleys 5B and the wire-fixing parts 14.

As illustrated in FIG. 15, the wire 11 for a first guide and the wire 12 for a second guide are inserted between the wire insertion parts 21b provided in the distal end surface 21a of the elongated member 21 and the wire insertion parts 21b of the first plate-shaped part 44f of the distal-side turning body 44 within the first joint 43A.

The wire 11 for a first guide and the wire 12 for a second guide are separately engaged with the respective pulley grooves 45c of the proximal-side pulley 5A and the distal-side pulley 45B, which face each other in the radial direction, in a reversed S-shape.

The wire 11 for a first guide and the wire 12 for a second guide are extended in the direction along the longitudinal axis O from the wire insertion parts 21b of the distal end surface 21a at positions (illustrated lower sides) shifted in the Y2 direction with respect to the longitudinal axis O. Then, these wires are wound in the Y1 direction along the respective pulley grooves 5c of the proximal-side pulley 5A and the distal-side pulley 45B and are wired so as to intersect the longitudinal axis O. Then, these wires are wound out in the direction along the longitudinal axis O, and are inserted through the wire insertion parts 21b of the first plate-shaped part 44f at the positions shifted in the Y1 direction with respect to the longitudinal axis O.

As illustrated in FIGS. 14A and 14B, the second joint 43B has a configuration in which the proximal-side support 13 of the joint part 33 of the first modification example of the aforementioned first embodiment is replaced with the proximal-side support 53B.

In the proximal-side support 53B, the proximal-side support 13 of the aforementioned first embodiment is fixed to the distal end surface 44a of the first plate-shaped part 44f of the distal-side turning body 44 of the first joint 43A.

However, the posture of the proximal-side support 53B, the first side surface 13b and the second side surface 13c is a posture orthogonal to the first side surface 13b and the second side surface 13c of the proximal-side support 53A of the first joint 43A, the second side surface 13c is arranged in the Y1 direction, and the first side surface 13b is arranged in the Y2 direction.

For this reason, the second joint 43B is a bending joint that turns in the X1 direction and the X2 direction.

Next, a switching operation between the drivable state and the relaxation state about the operation of the medical manipulator 41 having such a configuration will mainly be described.

Figure 16:
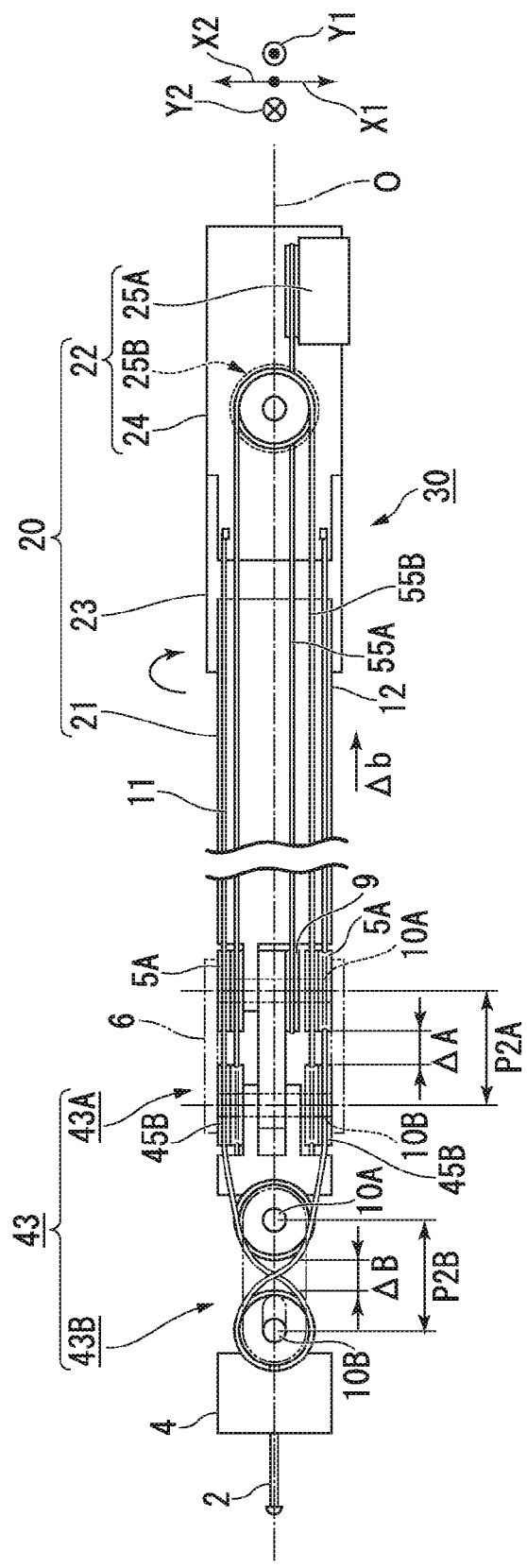
FIG. 16 is an operation explanatory view of the medical manipulator of the second embodiment of the invention.

FIG. 16 is an operation explanatory view of the medical manipulator of the second embodiment of the invention.

Since the medical manipulator 41 includes the treatment part 2, it is possible to perform a treatment based on remote manipulation on a treatment target region in the drivable state, similar to the medical manipulator 1 of the aforementioned first embodiment.

However, the bending obtained by combining the turning of the joint part 43 of the medical manipulator 41 in the Y1 and Y2 directions with respect to the longitudinal axis O with the turning of the joint part 43 in the X1 and X2 directions orthogonal to the Y1 and Y2 directions is possible by the combination of the turning motions of the first joint 43A and the second joint 43B.

Also in the medical manipulator 41, in order to include the position-adjusting part 23 and the stopper part 29, as illustrated in FIG. 16, similar to the medical manipulator 1 of the aforementioned first embodiment, the elongated member 21 and the support 24 can be relatively moved along the longitudinal axis O, and the relaxation state can be formed if the elongated member 21 is brought close to the support 24, for example, by the distance Δb.

In that case, in the present embodiment, the driving wire 55A is wound around the driving force input part 9 supported by the first turning shaft 10A of the first joint 43A that moves together with the elongated member 21. Accordingly, the inter-axial distance between the first turning shaft 10A and the driving shaft 25a of the drive motor 25A becomes short, and similar to the driving wire 15 of the aforementioned first embodiment, the driving wire 55A is relaxed.

Then, a gap ΔA is formed between the proximal-side pulley 5A and the distal-side pulley 45B of the first joint 43A by moving the distal-side turning body 44 to the elongated member 21 side by a distance smaller than the distance Δb. That is, the first turning shaft 10A of the first joint 43A that moves together with the distal-side turning body 44 is moved to the elongated member 21 side by a distance Δb−ΔA.

Since the driving wire 55B is wound around the driving force input part 9 supported by the first turning shaft 10A of the second joint 43B, the inter-axial distance between the first turning shaft 10A and the driving shaft 25a of the drive motor 25B reaches a second inter-axial distance P2A longer than the first inter-axial distance P1 by ΔA, and similar to the driving wire 15 of the aforementioned first embodiment, the driving wire 55B is relaxed.

Then, a gap ΔB is formed between the proximal-side pulley 5A and the distal-side pulley 45B of the second joint 43B by moving the distal-side turning body 4 of the second joint 43B to the elongated member 21 side by a distance smaller than the distance Δb−ΔA. That is, the first turning shaft 10A of the second joint 43B that moves together with the distal-side turning body 4 is moved to the elongated member 21 side by a distance Δb−ΔA−ΔB. Accordingly, the inter-axial distance between the first turning shaft 10A and the second turning shaft 10B of the second joint 43B reaches a second inter-axial distance P2B that is longer than the first inter-axial distance P1 by the gap ΔB.

The distal end 11a of the wire 11 for a first guide and the distal end 12a of the wire 12 for a second guide are fixed to the distal-side pulley 5B supported by the second turning shaft 10B of the second joint 43B, and the wire 11 for a first guide and the wire 12 for a second guide are stretched between the distal-side pulley 5B and the support 24. For this reason, the distance between the first turning shaft 10A and the support 24 becomes short by Δb−AA−AB, and the wire 11 for a first guide and the wire 12 for a second guide are relaxed.

In this way, in the medical manipulator 41, the driving wires 55A and 55B that are driving wire members of the first joint 43A and the second joint 43B, and the wire 11 for a first guide and the wire 12 for a second guide that are guide wires, can be all relaxed using the position-adjusting part 23, and all of engagements between the respective driving force input parts 9, the respective proximal-side pulleys 5A, and the distal-side pulleys 45B and 5B can be released.

In such a relaxation state, similar to the aforementioned first embodiment, gaps are formed within the first joint 43A and the second joint 43B, and for example, the cleaning work of inserting a brush becomes simple. Additionally, in the first joint 43A and the second joint 43B, a cleaning agent reliably runs on the surfaces of the respective members, there is no cleaning leakage, and cleaning can be rapidly and reliably performed.

Third Embodiment

Next, a medical manipulator of a third embodiment of the invention will be described.

Figure 17A:
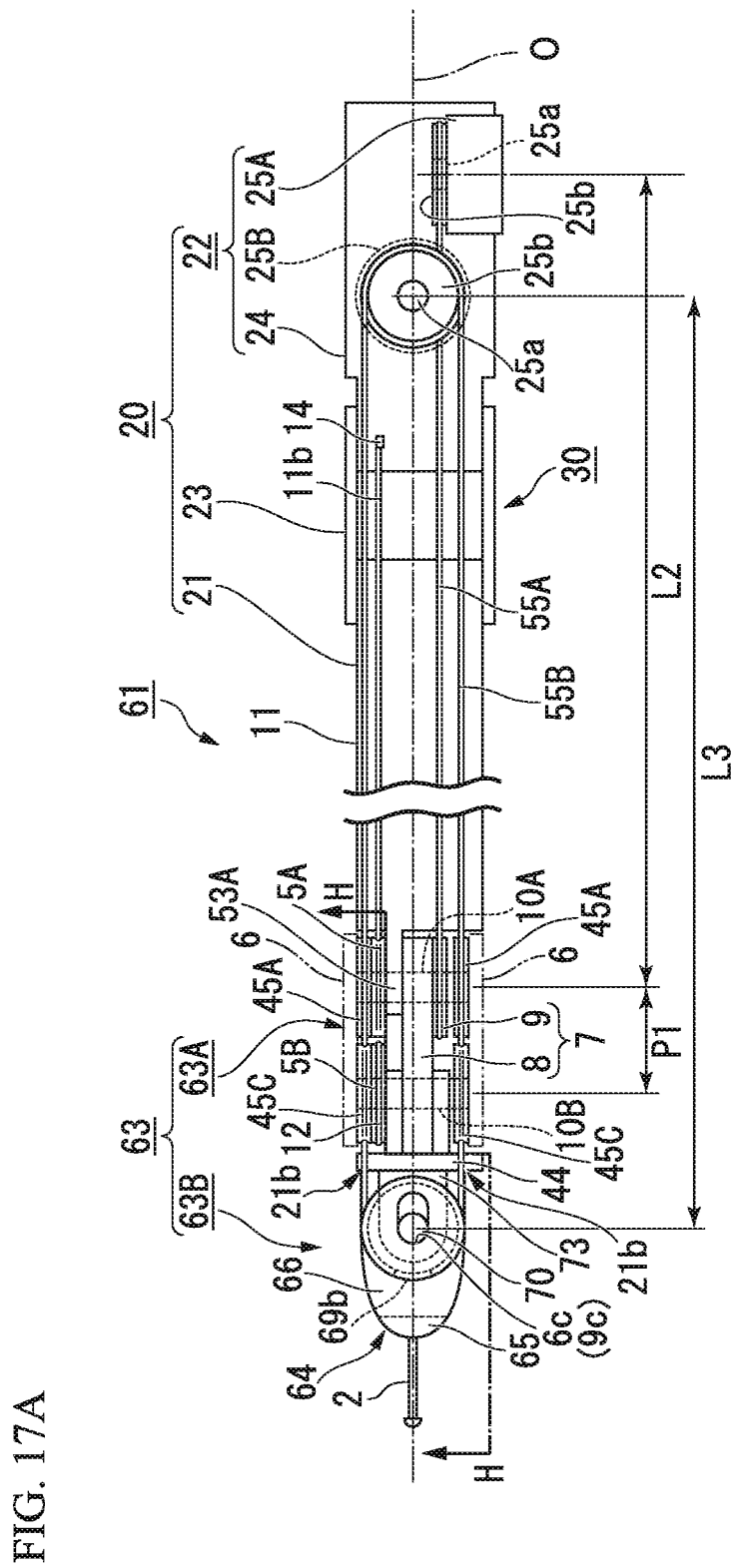
FIG. 17A is a schematic view illustrating the configuration of a medical manipulator of a third embodiment of the invention.
Figure 17B:
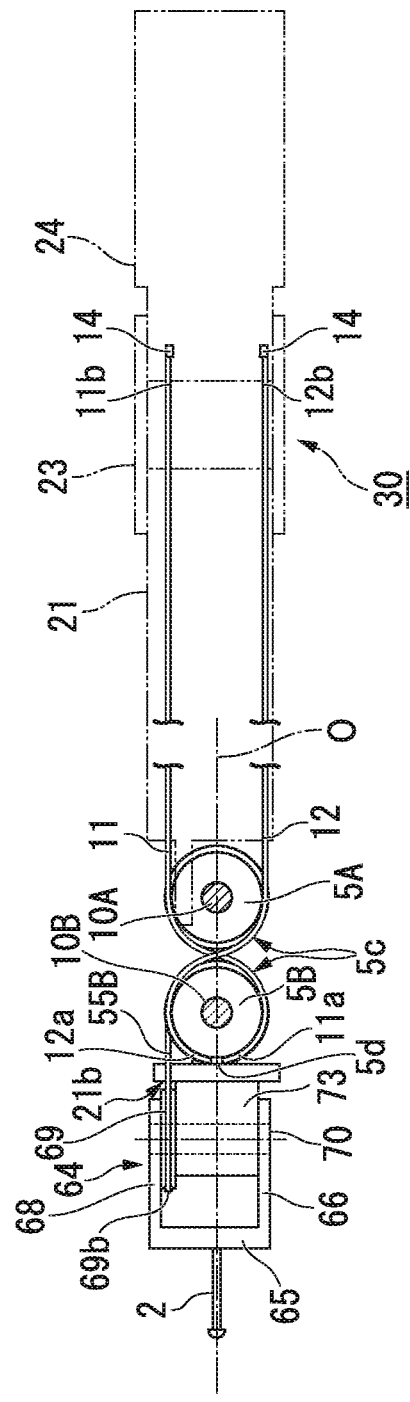
FIG. 17B is an H-H sectional view of FIG. 17A.
Figure 18:
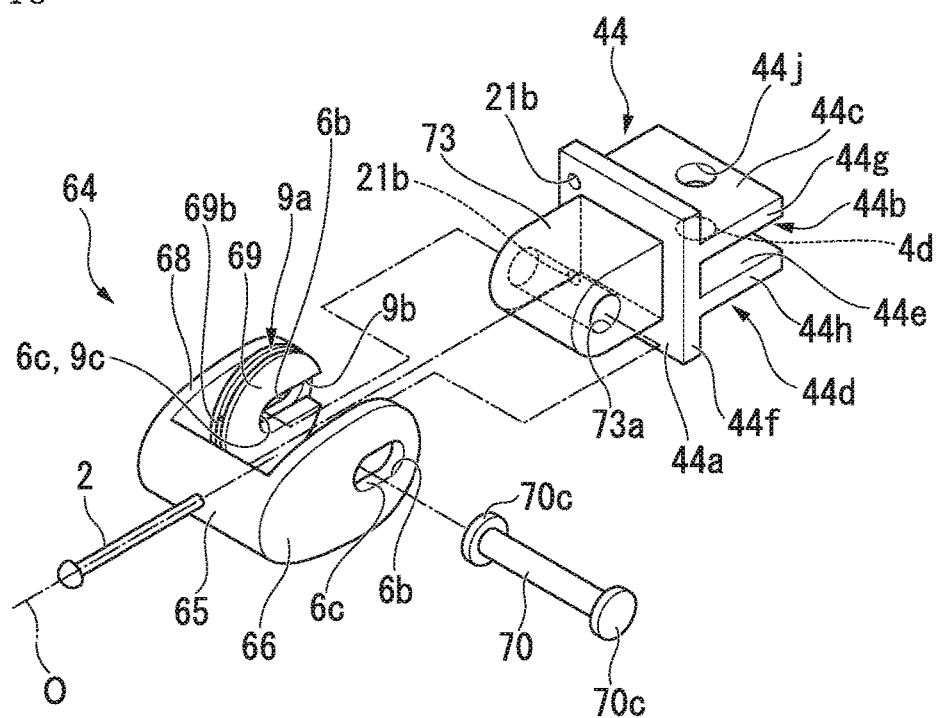
FIG. 18 is a schematic exploded perspective view illustrating the configuration of principal parts of a joint part of the medical manipulator of the third embodiment of the invention.

FIG. 17A is a schematic view illustrating the configuration of the medical manipulator of the third embodiment of the invention. FIG. 17B is an H-H sectional view in FIG. 17A. FIG. 18 is a schematic exploded perspective view illustrating the configuration of principal parts of a joint part of the medical manipulator of the third embodiment of the invention.

As illustrated in FIGS. 17A and 17B, a medical manipulator 61 of the present embodiment includes a joint part 63 constituted of a first joint 63A (first unit joint) that is a bending joint and a second joint 63B (second unit joint) that is a turning joint instead of the joint part 43 of the medical manipulator 41 of the aforementioned second embodiment.

That is, the medical manipulator 61 is an example in which the joint part is formed by coupling the two unit joints in series.

As illustrated in FIG. 1, the medical manipulator 61 can be used as a portion of the medical system 100 instead of the medical manipulator 1 of the aforementioned first embodiment. Hereinafter, differences from the aforementioned second embodiment will mainly be described.

In addition, in the medical manipulator 61, the joint part 63 is turnable and bendable in biaxial directions, and the length thereof in the direction along the longitudinal axis O of the body part 20 is changeable by the position-adjusting part 23, similar to the aforementioned second embodiment. Thus, also in the present embodiment, similar to the aforementioned second embodiment, a state where the driving of the joint part 63 is possible is referred to as the drivable state, and a state where the engagement between members used for driving in the joint part 63 is released and the driving is impossible is referred to as the relaxation state. In the following description, unless particularly mentioned in describing the positional relationship of the respective members in the drivable state, as illustrated in FIGS. 17A and 17B, description will be made on the basis of a state where the joint part 63 does not turn with respect to the longitudinal axis O.

The first joint 63A does not include a set of proximal-side pulley 5A and distal-side pulley 45B around which the wire 12 for a second guide is wound among the two sets of distal-side pulleys 45B and proximal-side pulleys 5A of the first joint 43A of the aforementioned second embodiment, and replaces the distal-side pulley 45B around which the wire 11 for a first guide is wound with the distal-side pulley 5B. However, the positions of the distal-side pulley 5B and the proximal-side pulley 5A are substituted with the positions of the distal-side idler pulley 45C and the proximal idler pulley 45A adjacent to each other.

In the first joint 63A, similar to the aforementioned first embodiment, the distal end 11a of the wire 11 for a first guide and the distal end 12a of the wire 12 for a second guide are fixed to the wire-fixing parts 5d of the distal-side pulley 5B. Additionally, the wire 11 for a first guide and the wire 12 for a second guide are wound around the respective pulley grooves 5c so that the wire 11 for a first guide and the wire 12 for a second guide intersect each other.

The proximal ends 11b and 12b of the wire 11 for a first guide and the wire 12 for a second guide are fixed to the support 24 via the wire-fixing part 14, similar to the aforementioned first embodiment.

For this reason, in the first joint 63A, the portion constituted of the proximal-side support 53A, the second coupling member 7, the distal-side turning body 44, the distal-side pulley 5B, and the proximal-side pulley 5A constitutes the bending joint having the same configuration as the joint part 3 of the aforementioned first embodiment.

In the drivable state, the inter-axial distance between the first turning shaft 10A of the first joint 63A and the driving shaft 25a of the drive motor 25A is L2.

The driving wires 55B are respectively wound around the respective proximal idler pulleys 45A and the respective distal-side idler pulleys 45C and inserted into the first joint 63A, similar to the aforementioned second embodiment.

As illustrated in FIG. 18, the second joint 63B includes a proximal-side support 73 that is fixed to the distal end surface 44a of the distal-side turning body 44 and has a shaft hole 73a extending in the direction orthogonal to the first turning shaft 10A and the second turning shaft 10B in the first joint 63A, a turning shaft 70 that is turnably supported by the shaft hole 73a, and a distal-side turning body 64 (rotating body) that has the treatment part 2 coupled to the distal side thereof.

The distal-side turning body 64 includes a distal end 65 that has the treatment part 2 coupled thereto and extends in the direction orthogonal to the longitudinal axis O, a pair of plate-shaped parts 66 and 68 that extend to the proximal side along the longitudinal axis O from both ends of the longitudinal direction of the distal end 65, and a driving force input part 69 that is provided in a surface that faces the pair of plate-shaped parts 66 and 68 in order to receive a driving force from the driving wire 55B.

The same sliding hole 6b for a bearing as the aforementioned first embodiment is provided to pass through the plate-shaped part 66 in the thickness direction. The longitudinal direction of the sliding hole 6b for a bearing in the plate-shaped part 66 coincides with the longitudinal axis O, and the bearing part 6c is formed in an inner peripheral surface near the distal end 65.

The plate-shaped part 68 has the same shape as the plate-shaped part 66. For this reason, the sliding hole 6b for a bearing is provided at a position that faces the sliding hole 6b for a bearing of the plate-shaped part 66, and the center of each bearing part 6c is coaxial with an axis orthogonal to the longitudinal direction.

The driving force input part 69 has a configuration in which a wire-fixing part 69b that fixes the driving wire 55B is added to the pulley groove 9a of the driving force input part 9 of the second coupling member 7.

A U-shaped groove 9b for a bearing of the driving force input part 69 opens within a range that overlaps the sliding hole 6b for a bearing of the plate-shaped part 68, and a bearing part 9c of the U-shaped groove 9b for a bearing is aligned with the bearing part 6c of the plate-shaped part 68.

The turning shaft 70 is inserted into the sliding hole 6b for a bearing and the U-shaped groove 9b for a bearing and is retained in the axial direction by retaining parts 70c provided at both ends of the turning shaft 70, in a state where the sliding hole 6b for a bearing of the plate-shaped part 66 and the U-shaped groove 9b for a bearing of the driving force input part 69 face the opening of the shaft hole 73a of the proximal-side support 73, respectively.

Accordingly, the distal-side turning body 64 is coupled to the proximal-side support 73 so as to be turnable around the turning shaft 70.

As illustrated in FIGS. 17A and 17B, the driving wire 55B wound around the driving pulley 25b of the drive motor 25B is introduced into the second joint 63B through the wire insertion part 21b provided to pass through the first plate-shaped part 44f of the distal-side turning body 44.

The driving wire 55B is wound around the pulley groove 9a of the driving force input part 69, and is fixed to the wire-fixing part 69b.

In the drivable state, the turning shaft 70 of the second joint 63B abuts against the bearing parts 6c and 9c (refer to FIG. 18) of the distal-side turning body 64. In this state, the inter-axial distance between the turning shaft 70 and the driving shaft 25a of the drive motor 25B is L3. In this case, a tension that allows a driving force to be transmitted to the driving force input part 69 is generated on the driving wire 55B, and the bearing parts 6c and 9c of the distal-side turning body 64 are pressed against the turning shaft 70 by the driving wire 55B.

According to the first joint 63A and the second joint 63B having such a configuration, the distal-side turning body 44 of the first joint 63A can be bent similar to the second embodiment by driving the drive motors 25A and 25B in the drivable state, and the distal-side turning body 64 and the treatment part 2 fixed thereto can be turned by driving the second joint 63B in a direction orthogonal to this bending direction. Additionally, similar to the aforementioned second embodiment, switching to the relaxation state can be performed by bringing the elongated member 21 close to the support 24, using the position-adjusting part 23.

That is, if the elongated member 21 is brought close to the support 24, the inter-axial distance between the first turning shaft 10A of the first joint 63A and the driving shaft 25a of the drive motor 25A becomes shorter than L2, and the inter-axial distance between the turning shaft 70 and the driving shaft 25a of the drive motor 25B becomes shorter than L3. Accordingly, the driving wires 55A and 55B are relaxed, and the engaged state between the driving force input parts 9 and 69 is released.

In that case, by adjusting the movement distances of the distal-side turning bodies 4 and 44 to thereby make the inter-axial distance between the first turning shaft 10A and the second turning shaft 10B in the first joint 43A greater than the first inter-axial distance L1, a gap can be formed between the proximal-side pulley 5A and the distal-side pulley 5B and the engagement between the wire 11 for a first guide and the wire 12 for a second guide can be released.

Accordingly, the medical manipulator 61 can be more efficiently and more easily cleaned.

Fourth Embodiment

Next, a medical manipulator of a fourth embodiment of the invention will be described.

Figure 19A:
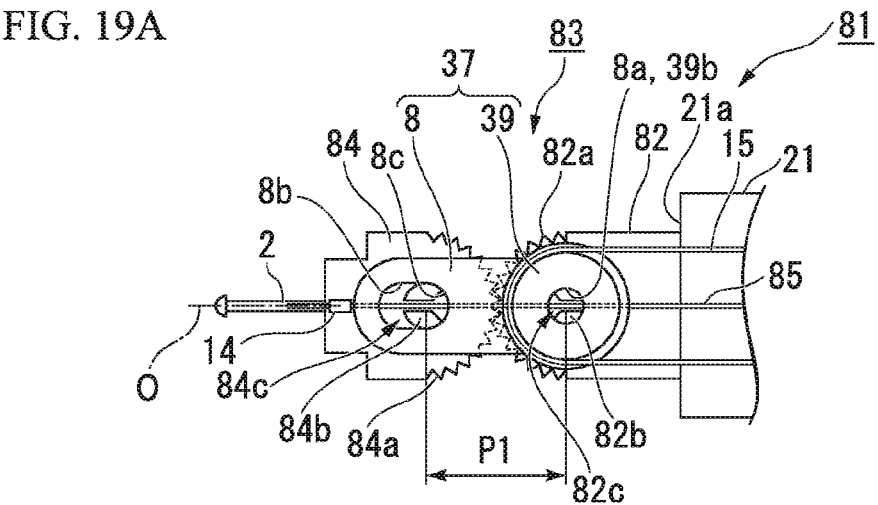
FIG. 19A is a schematic front view illustrating the configuration of principal parts of a medical manipulator of a fourth embodiment of the invention.
Figure 19B:
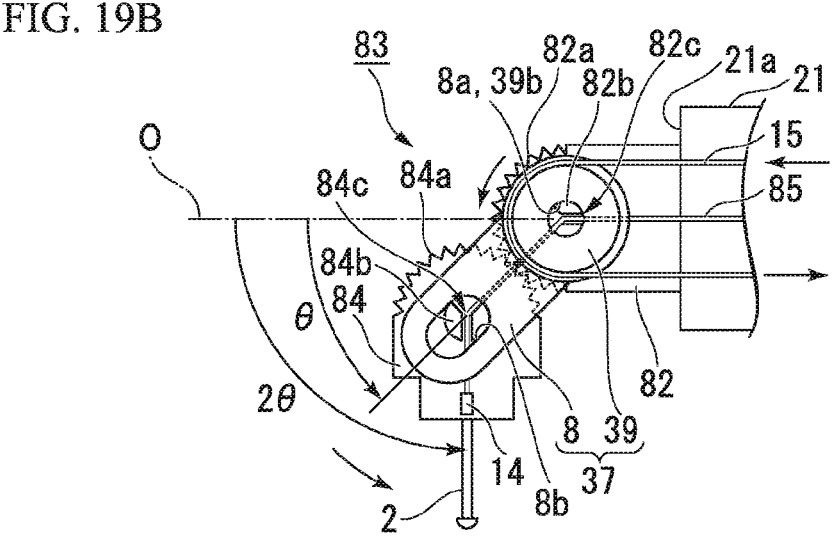
FIG. 19B is a schematic operation explanatory view illustrating the configuration of the principal parts of the medical manipulator of the fourth embodiment of the invention.
Figure 19C:
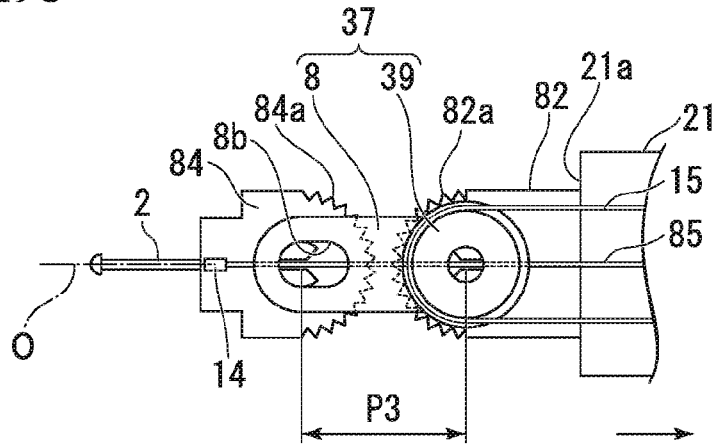
FIG. 19C is a schematic operation explanatory view illustrating the configuration of the principal parts of the medical manipulator of the fourth embodiment of the invention.

FIG. 19A is a schematic front view illustrating the configuration of principal parts of the medical manipulator of the fourth embodiment of the invention. FIGS. 19B and 19C are operation explanatory views of the medical manipulator of the fourth embodiment of the invention.

As illustrated in FIG. 19A, a medical manipulator 81 of the present embodiment includes a joint part 83 that is a bending joint instead of the joint part 3 of the medical manipulator 1 of the aforementioned first embodiment.

As illustrated in FIG. 1, the medical manipulator 81 can be used as a portion of the medical system 100 instead of the medical manipulator 1 of the aforementioned first embodiment.

Hereinafter, differences from the aforementioned first embodiment will mainly be described.

In addition, in the medical manipulator 81, the joint part 83 is bendable, and the length thereof in the direction along the longitudinal axis O of the body part 20 is changeable by the position-adjusting part 23, similar to the aforementioned first embodiment. Thus, also in the present embodiment, similar to the aforementioned first embodiment, a state where the driving of the joint part 83 is possible is referred to as the drivable state, and a state where the engagement between members used for driving in the joint part 83 is released and the driving is impossible is referred to as the relaxation state. In the following description, unless particularly mentioned in describing the positional relationship of the respective members in the drivable state, as illustrated in FIG. 19A, description will be made on the basis of a state where the joint part 83 does not turn with respect to the longitudinal axis O.

As illustrated in FIG. 19A, the joint part 83 includes a proximal-side support 82, a distal-side turning body 84, and the same second coupling member 37 as that of the first modification example of the aforementioned first embodiment.

The proximal-side support 82 is fixed to the distal end surface 21a of the elongated member 21 on the proximal side thereof, and has a gear part 82a (first guide part) with the pitch diameter P1 formed in a circular-arc range at the distal end thereof.

A first turning shaft 82b, which is turnably fitted to the circular holes 8a and 39b for a bearing of the second coupling member 37, is erected at a position coaxial with the pitch circle of the gear part 82a from the side surface of the proximal-side support 82.

A wire insertion groove (first wire insertion part) 82c through which a wire 85 for a guide (guide wire) to be described below is insertable along the longitudinal axis O through the axial center of the first turning shaft 82b is formed in the first turning shaft 82b.

The wire insertion groove 82c is formed in a linear shape having a diameter substantially equal to the wire diameter of the wire 85 for a guide at a position closer to the distal side than the axial center of the first turning shaft 82b, and is formed in a sector shape of which the groove width increases gradually, at a position closer to the proximal side than the axial center of the first turning shaft 82b. The central angle of the sector shape is set to a size such that the wire 85 for a guide does not hinder turning, according to the range of a turning angle at which the second coupling member 37 turns around the first turning shaft 82b with the bending of the joint part 83.

The distal-side turning body 84 has the treatment part 2 coupled to the distal side thereof, and has the same gear part (the first guide part) 84a as the proximal-side support 82 formed in a circular-arc range at the proximal end thereof.

A second turning shaft 84b, which is turnably fitted to the sliding hole 8b for a bearing of the second coupling member 37, is erected at a position coaxial with the pitch circle of the gear part 84a from the side surface of the distal-side turning body 84.

A wire insertion groove (second wire insertion part) 84c through which a wire 85 for a guide (guide wire) is insertable along the longitudinal axis O through the axial center of the second turning shaft 84b is formed in the second turning shaft 84b.

The wire insertion groove 84c is formed in a linear shape having a diameter substantially equal to the wire diameter of the wire 85 for a guide at a position closer to the distal side than the axial center of the second turning shaft 84b, and is formed in a sector shape of which the groove width increases gradually, at a position closer to the proximal side than the axial center of the second turning shaft 84b.

Such proximal-side support 82 and distal-side turning body 84 are coupled together by the first turning shaft 82b being inserted through the circular holes 8a and 39b for a bearing of the second coupling member 37 and by the second turning shaft 84b being inserted through the sliding hole 8b for a bearing of the second coupling member 37. Although illustration is omitted because FIG. 19A is a schematic view, the second coupling member 37 and the first turning shaft 82b and the second turning shaft 84b are retained.

In the present embodiment, the driving wire 15 is wound around the driving force input part 39 of the second coupling member 37.

The wire 85 for a guide has one end extended from the wire insertion groove 84c of the second turning shaft 84b is fixed to the distal-side turning body 84 via the wire-fixing part 14.

Although the other end of the wire 85 for a guide is not particularly illustrated, the other end is fixed to the support 24 via the wire-fixing part 14, similar to the wire 11 for a first guide of the aforementioned first embodiment.

The length of the wire 85 for a guide is a length at which a tension is generated when the inter-axial distance between the first turning shaft 82b and the second turning shaft 84b reaches P 1.

In the joint part 83, the wire insertion grooves 82c and 84c constitute a wire insertion part capable of stretching the wire 85 for a guide between the axial centers of the first turning shaft 82b and the second turning shaft 84b.

According to such a joint part 83, as illustrated in FIG. 19B, a driving force is transmitted from the driving wire 15 to the driving force input part 39 by driving the drive motor 25 (not illustrated) to turn the driving pulley 25b (not illustrated), and the driving force input part 39 turns in the same direction as the driving pulley 25b. Accordingly, the second coupling member 37 is turned, for example, by the angle θ around the first turning shaft 82b.

In this case, since the gear part 84a meshes and engages with the gear part 82a, the second turning shaft 84b of the distal-side turning body 84 rotates on its own axis by the angle θ within the bearing part 8c of the sliding hole 8b for a bearing and turns on the pitch circle of the gear part 82a of the proximal-side support 82 around the first turning shaft 82b, and the joint part 83 is bent.

Accordingly, the orientation of the distal-side turning body 4 fixed to the distal-side turning body 84 turns by the angle 2θ with respect to the longitudinal axis O.

In order to bring the medical manipulator 81 into the relaxation state, as illustrated in FIG. 19C, the elongated member 21 is brought close to the support 24 (not illustrated), using the position-adjusting part 23 (not illustrated), similar to the aforementioned first embodiment. Accordingly, the inter-axial distance between the first turning shaft 82b and the second turning shaft 84b reaches the greater second inter-axial distance P3 than the first inter-axial distance P1.

For this reason, the engagement between the gear parts 82a and 84a is released and thus a gap is formed, and the wire 85 for a guide is relaxed. Additionally, the driving wire 15 is also relaxed and a gap is also formed between the driving force input part 39 and the driving wire 15.

For this reason, the medical manipulator 81 can be more efficiently and more easily cleaned, similar to the aforementioned first embodiment.

Fifth Embodiment

Next, a medical manipulator of a fifth embodiment of the invention will be described.

Figure 20A:
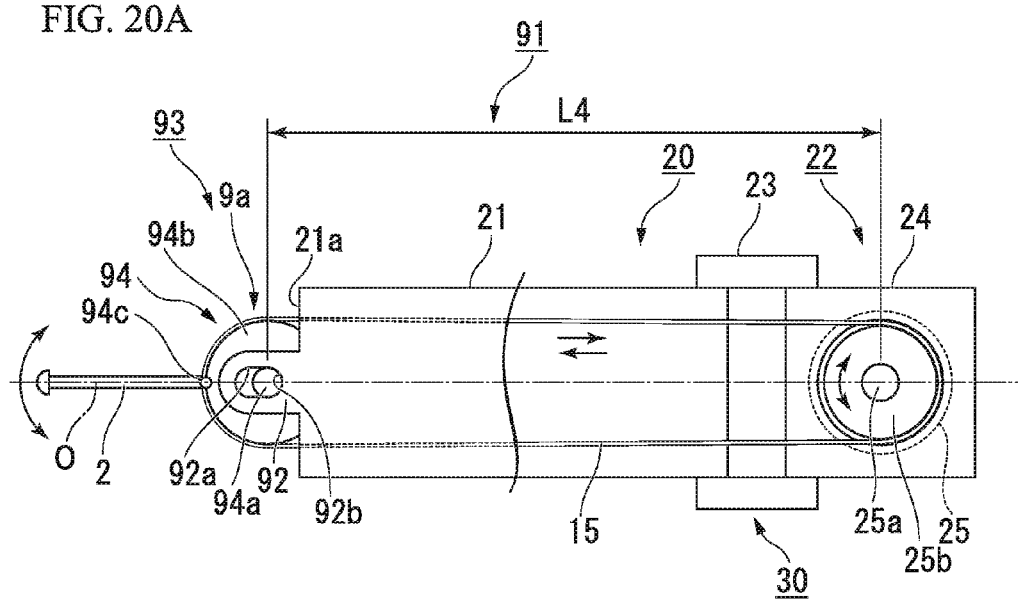
FIG. 20A is a schematic front view illustrating the configuration of principal parts of a medical manipulator of a fifth embodiment of the invention.
Figure 20B:
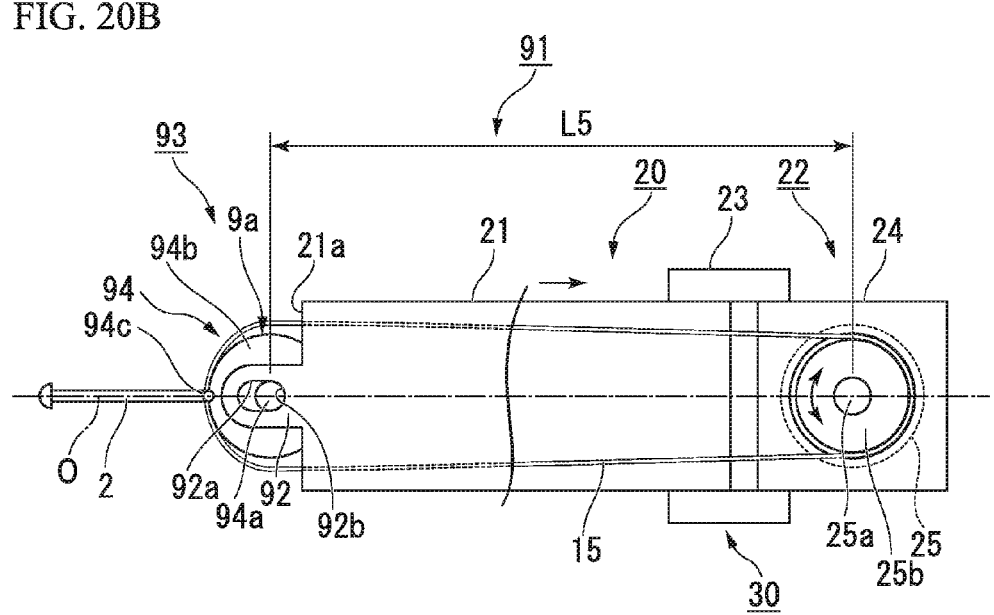
FIG. 20B is a schematic operation explanatory view illustrating the configuration of the principal parts of the medical manipulator of the fifth embodiment of the invention.

FIG. 20A is a schematic front view illustrating the configuration of the medical manipulator of the fifth embodiment of the invention. FIG. 20B is an operation explanatory view of the medical manipulator of the fifth embodiment of the invention.

As illustrated in FIG. 20A, a medical manipulator 91 of the present embodiment includes a joint part 93 that is a turning joint instead of the joint part 3 of the medical manipulator 1 of the aforementioned first embodiment.

As illustrated in FIG. 1, the medical manipulator 91 can be used as a portion of the medical system 100 instead of the medical manipulator 1 of the aforementioned first embodiment.

Hereinafter, differences from the aforementioned first embodiment will mainly be described.

In addition, in the medical manipulator 91, the joint part 93 is turnable, and the length thereof in the direction along the longitudinal axis O of the body part 20 is changeable by the position-adjusting part 23, similar to the aforementioned first embodiment. Thus, also in the present embodiment, similar to the aforementioned first embodiment, a state where the driving of the joint part 93 is possible is referred to as the drivable state, and a state where the engagement between members used for driving in the joint part 93 is released and the driving is impossible is referred to as the relaxation state. In the following description, unless particularly mentioned in describing the positional relationship of the respective members in the drivable state, as illustrated in FIG. 20A, description will be made on the basis of a state where the joint part 93 does not turn with respect to the longitudinal axis O.

As illustrated in FIG. 20A, in the medical manipulator 91, the joint part 93 includes a proximal-side support 92 and a distal-side turning body 94 (rotating body).

The proximal-side support 92 is fixed to the distal end surface 21a of the elongated member 21 on the proximal side thereof, and includes a sliding hole 92a for a bearing in an oval shape in which a longitudinal direction runs along at the longitudinal axis O, on the distal side thereof.

A semicircular bearing part 92b is formed on the proximal side of the sliding hole 92a for a bearing.

The inter-axial distance between the center of the bearing part 92b and the driving shaft 25a of the drive motor 25 is L4 (third inter-axial distance) in the drivable state.

The treatment part 2 is coupled to the distal side of the distal-side turning body 94, and the driving force input part 94b, which is a pulley part (fixing pulley) having the pulley groove 9a for winding the driving wire 15 therearound at the outer periphery thereof, is fixed to a proximal end of the distal-side turning body 94.

A turning shaft 94a (third turning shaft), which is inserted through the sliding hole 92a for a bearing of the proximal-side support 92 and turnably fitted to the bearing part 92b at a position coaxial with the pulley groove 9a, is erected from a central part of the driving force input part 94b.

A wire-fixing part 94c that fixes the distal-side turning body 94 and the driving wire 15 is provided on the pulley groove 9a on the distal side of the driving force input part 94b. As a fixing method, for example, crimping fixation is used.

The driving wire 15 has a length such that a tension capable of transmitting a driving force is generated in the drivable state, and is wound in an oval shape around the driving force input part 94b and the driving pulley 25b (driving turning member) provided in the proximal-side device section 22.

The driving wire 15 is fixed to the distal-side turning body 94 by the wire-fixing part 94c.

According to such a medical manipulator 91, a driving force is transmitted from the driving wire 15 to the driving force input part 94b by driving the drive motor 25 (not illustrated) to turn the driving pulley 25b (not illustrated), and the driving force input part 94b turns in the same direction as the driving pulley 25b (refer to the arrow of FIG. 20A).

In order to bring the medical manipulator 91 into the relaxation state, as illustrated in FIG. 20B, the elongated member 21 is brought close to the support 24, using the position-adjusting part 23, similar the aforementioned first embodiment. The inter-axial distance between the center of the bearing part 92b of the proximal-side support 92 and the driving shaft 25a of the drive motor 25 is smaller L5 (fourth inter-axial distance) than the center distance L4.

For this reason, by appropriately shifting the turning shaft 94a in the range of the sliding hole 92a for a bearing, the engagement of the turning shaft 94a with the bearing part 92b is released, and the driving wire 15 is relaxed and the engagement between the pulley groove 9a and the driving wire 15 except the wire-fixing part 94c is released.

For this reason, the medical manipulator 91 can be more efficiently and more easily cleaned, similar to the aforementioned first embodiment.

Second Modification Example

Next, a medical manipulator of a modification example (second modification example) of the fifth embodiment of the invention will be described.

Figure 21A:
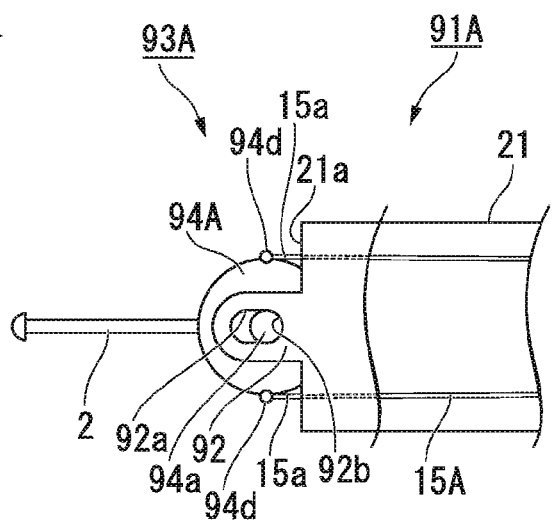
FIG. 21A is a schematic front view illustrating the configuration of principal parts of a medical manipulator of a modification example (second modification example) of the fifth embodiment of the invention.
Figure 21B:
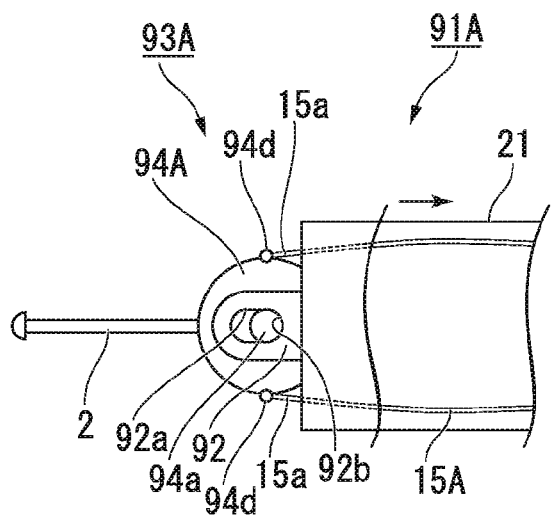
FIG. 21B is a schematic operation explanatory view illustrating the configuration of the principal parts of the medical manipulator of the modification example (second modification example) of the fifth embodiment of the invention.

FIG. 21A is a schematic front view illustrating the configuration of principal parts of the medical manipulator of the modification example (second modification example) of the fifth embodiment of the invention. FIG. 21B is an operation explanatory view of the medical manipulator of the modification example (second modification example) of the fifth embodiment of the invention.

As illustrated in FIG. 21A, the medical manipulator 91A of the present modification example includes a driving wire 15A (driving wire member) and a joint part 93A instead of the driving wire 15 and the joint part 93 of the medical manipulator 91 of the aforementioned fifth embodiment.

As illustrated in FIG. 1, the medical manipulator 91A can be used as a portion of the medical system 100 instead of the medical manipulator 1 of the aforementioned first embodiment.

Hereinafter, differences from the aforementioned fifth embodiment will mainly be described.

The driving wire 15A is constituted of one wire in which an intermediate part is wound around the driving pulley 25b of the drive motor 25 (not illustrated), and has wire ends 15a at both ends thereof.

The joint part 93A does not include the pulley groove 9a of the distal-side turning body 94 of the aforementioned fifth embodiment. Additionally, the joint part 93A includes a distal-side turning body 94A (rotating body) that has a driving force input part 94d for fixing the wire end 15a of the driving wire 15A at an outer peripheral part thereof, instead of the driving force input part 94b.

The fixing method of the wire end 15a in the driving force input part 94d is not particularly limited, and for example, fixing methods, such as crimping and welding, can be adopted.

The driving force input part 94d is provided at the outer peripheral part of the distal-side turning body 94A that sandwiches the turning shaft 94a therein. If the driving wire 15A is pulled to the proximal side, a moment around the turning shaft 94a is generated by a force acting on the driving force input part 94d, and a driving force is transmitted to the distal-side turning body 94A.

For this reason, according to such a medical manipulator 91A, the distal-side turning body 94A can be turned around the turning shaft 94a in the drivable state, similar to the aforementioned fifth embodiment.

Additionally, the medical manipulator 91A can be brought into the relaxation state, similar to the aforementioned fifth embodiment. However, in the present modification example, the driving wire 15A is not wound around the distal-side turning body 94A. Therefore, as illustrated in FIG. 21B, there is a difference in that the driving wire 15A is mainly relaxed inside the elongated member 21.

Third Modification Example

Next, a medical manipulator of a modification example (third modification example) of the fifth embodiment of the invention will be described.

Figure 22A:
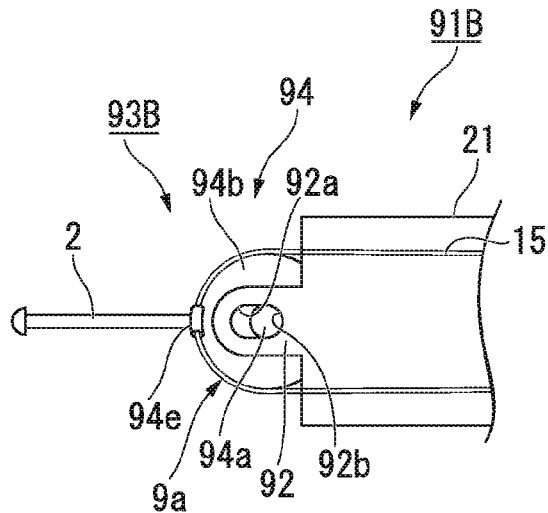
FIG. 22A is a schematic front view illustrating the configuration of principal parts of a medical manipulator of a modification example (third modification example) of the fifth embodiment of the invention.
Figure 22B:
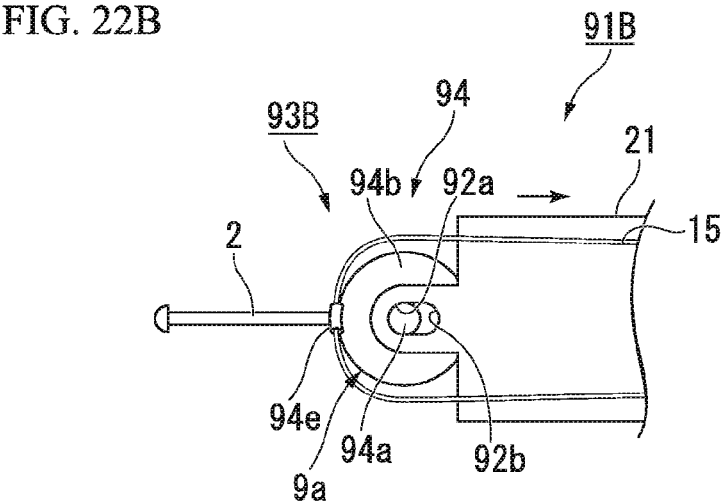
FIG. 22B is a schematic operation explanatory view illustrating the configuration of the principal parts of the medical manipulator of the modification example (third modification example) of the fifth embodiment of the invention.

FIG. 22A is a schematic front view illustrating the configuration of principal parts of the medical manipulator of the modification example (third modification example) of the fifth embodiment of the invention. FIG. 22B is an operation explanatory view of the medical manipulator of the modification example (third modification example) of the fifth embodiment of the invention.

As illustrated in FIG. 22A, a medical manipulator 91B of the present modification example includes a joint part 93B instead of the joint part 93 of the medical manipulator 91 of the aforementioned fifth embodiment.

As illustrated in FIG. 1, the medical manipulator 91B can be used as a portion of the medical system 100 instead of the medical manipulator 1 of the aforementioned first embodiment.

Hereinafter, differences from the aforementioned fifth embodiment will mainly be described.

The joint part 93B includes a wire insertion part 94e instead of the wire-fixing part 94c of the distal-side turning body 94 of the aforementioned fifth embodiment.

The wire insertion part 94e is a tubular member through which the driving wire 15 is insertable. The driving wire 15 is configured so as not to be detached from the pulley groove 9a by the wire insertion part 94e in the relaxation state.

According to the present modification example, in the drivable state, the distal-side turning body 94 can be turned, similar to the aforementioned fifth embodiment.

However, in the present modification example, the driving wire 15 is not fixed to the driving force input part 94b. Therefore, an example in which a driving force is transmitted to the driving force input part 94b only by the frictional force of the driving wire 15 is provided.

Additionally, as illustrated in FIG. 22B, according to the present modification example, the medical manipulator 91B can be brought into the relaxation state, similar to the aforementioned fifth embodiment.

However, in the present modification example, the driving wire 15 is not fixed to the driving force input part 94b. Therefore, when the driving wire 15 is returned to the drivable state again, the direction of the treatment part 2 may not become the same direction as in the drivable state before being brought into the relaxation state. In this case, if required, positional adjustment may be performed by performing the turning of the distal-side turning body 94 in the drivable state.

Fourth Modification Example

Next, a medical manipulator of a modification example (fourth modification example) of the fifth embodiment of the invention will be described.

Figure 23A:
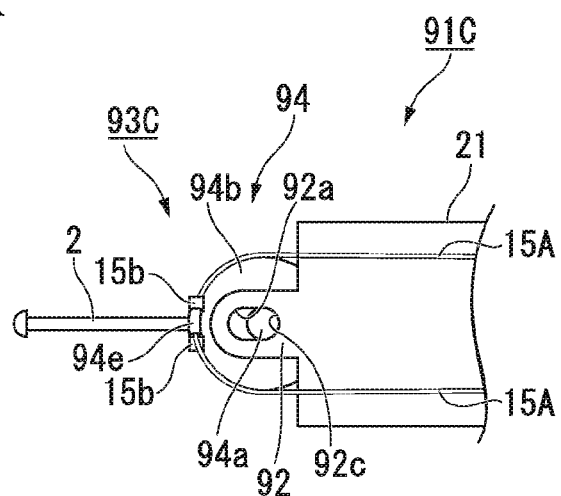
FIG. 23A is a schematic front view illustrating the configuration of principal parts of a medical manipulator of a modification example (fourth modification example) of the fifth embodiment of the invention.
Figure 23B:
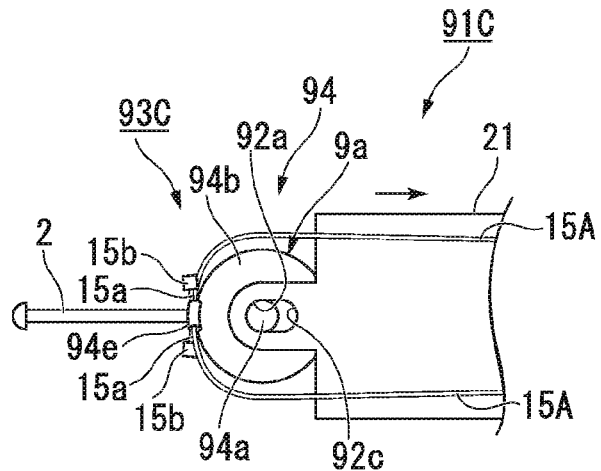
FIG. 23B is a schematic operation explanatory view illustrating the configuration of the principal parts of the medical manipulator of the modification example (fourth modification example) of the fifth embodiment of the invention.

FIG. 23A is a schematic front view illustrating the configuration of principal parts of the medical manipulator of the modification example (fourth modification example) of the fifth embodiment of the invention. FIG. 23B is an operation explanatory view of the medical manipulator of the modification example (fourth modification example) of the fifth embodiment of the invention.

As illustrated in FIG. 23A, the medical manipulator 91C of the present modification example includes the same driving wire 15A (power transmission member) as that of the aforementioned third modification example and a joint part 93C instead of the driving wire 15 and the joint part 93 of the medical manipulator 91 of the aforementioned fifth embodiment.

As illustrated in FIG. 1, the medical manipulator 91C can be used as a portion of the medical system 100 instead of the medical manipulator 1 of the aforementioned first embodiment.

Hereinafter, differences from the aforementioned fifth embodiment will mainly be described.

The joint part 93C includes the same wire insertion part 94e as that of the fourth aforementioned modification example instead of the wire-fixing part 94c of the distal-side turning body 94 of the aforementioned fifth embodiment.

In the present modification example, the respective wire ends 15a of the driving wire 15A are inserted through the wire insertion part 94e from mutually opposite directions. A larger-diameter part 15b having a size capable of being locked to and retained by an opening of the wire insertion part 94e is formed in each wire end 15a.

For this reason, as illustrated in FIG. 23A, the position of each wire end 15a with respect to the driving force input part 94b is fixed in a state where each larger-diameter part 15b has been locked to the opening of the wire insertion part 94e by the tension of the driving wire 15A in the drivable state.

In contrast, as illustrated in FIG. 23B, when being brought into the relaxation state similar to the aforementioned fifth embodiment, it is possible to extend the driving wire to the outside of the wire insertion part 94e depending on the amount of relaxation. Therefore, since the engagements between the wire ends 15a, the larger-diameter parts 15b, and the wire insertion part 94e can also be altogether released in the relaxation state, cleaning is more easily performed.

Sixth Embodiment

Next, a medical manipulator of a sixth embodiment of the invention will be described.

Figure 24:
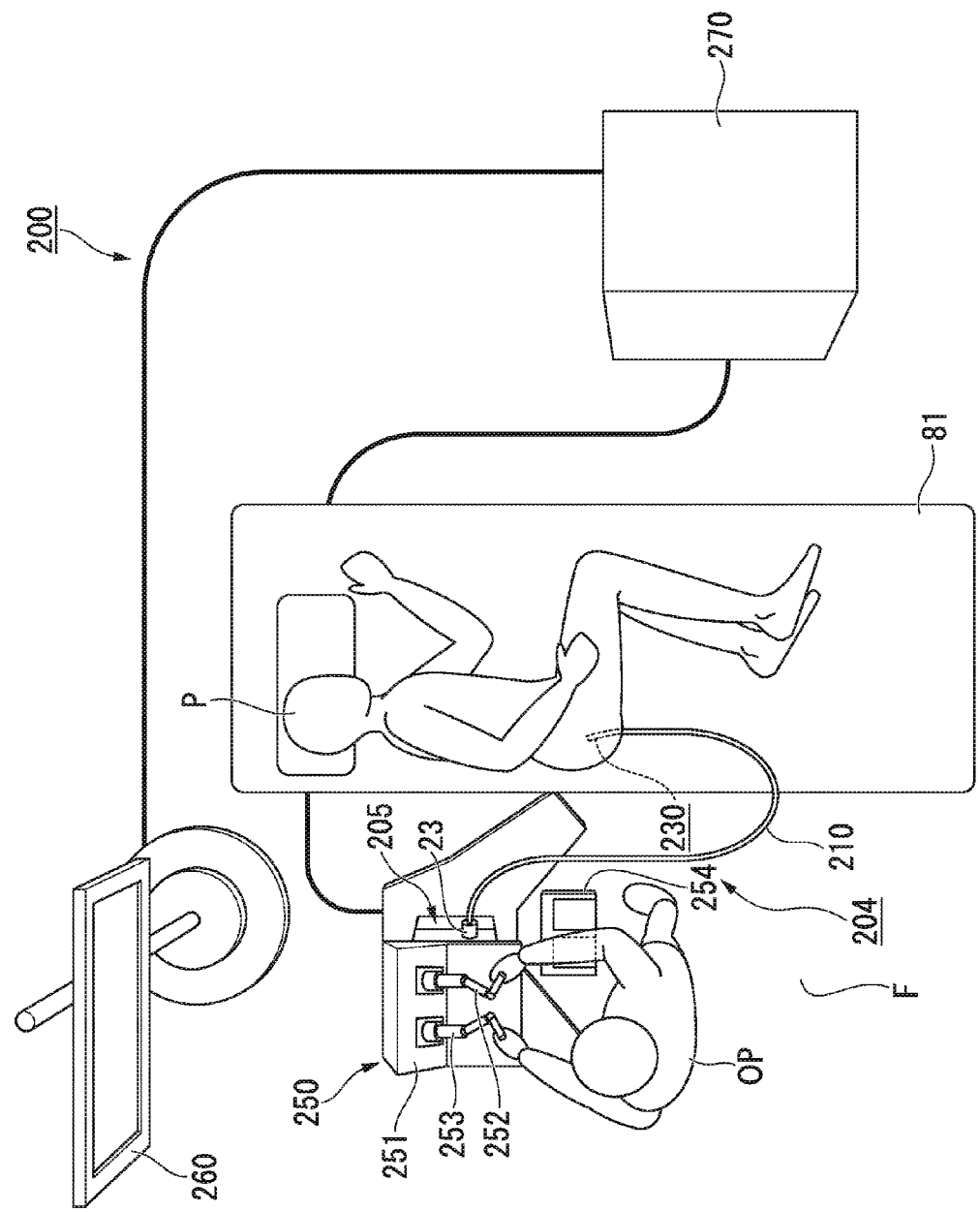
FIG. 24 is a schematic configuration view of a medical system including a medical manipulator of a sixth embodiment of the invention.
Figure 25:
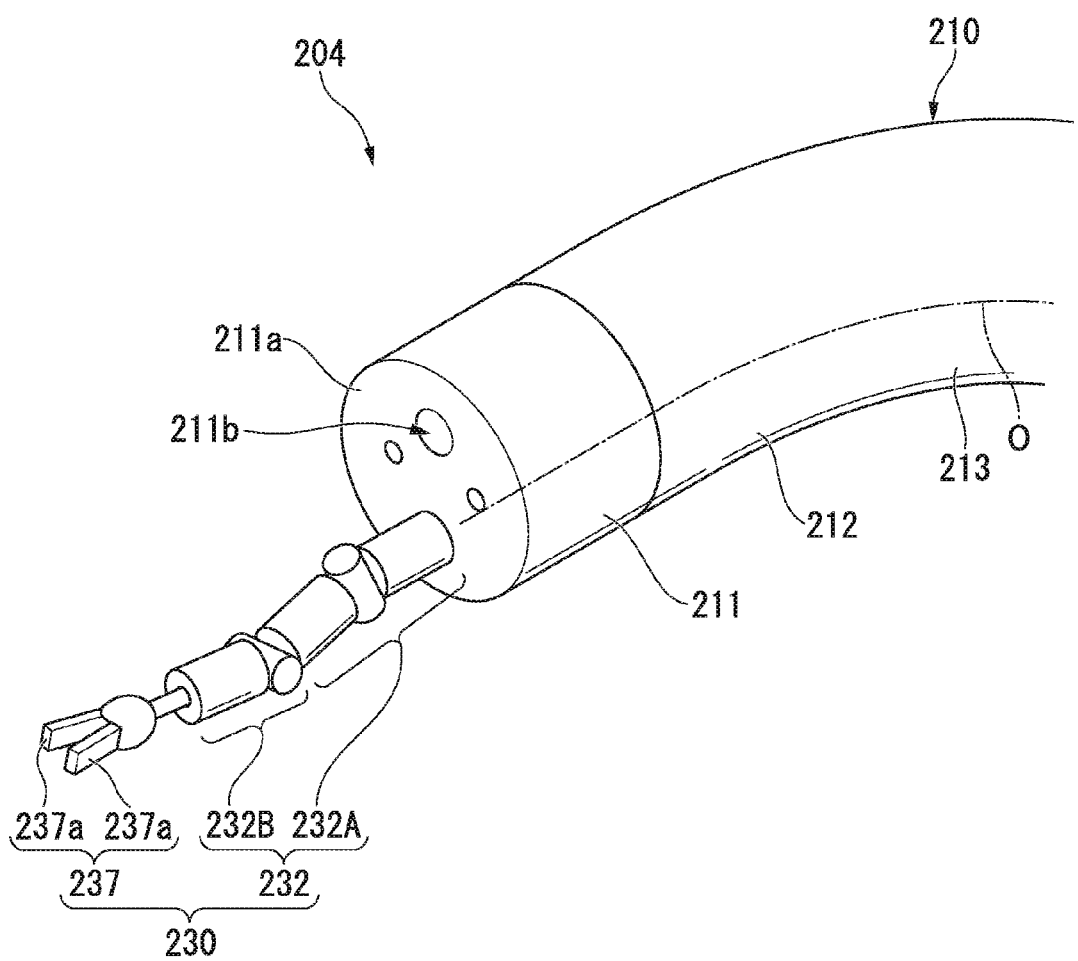
FIG. 25 is a schematic perspective view illustrating principal parts of the medical manipulator of the sixth embodiment of the invention.

FIG. 24 is a schematic configuration view of a medical system including the medical manipulator of the sixth embodiment of the invention. FIG. 25 is a schematic perspective view illustrating principal parts of the medical manipulator of the sixth embodiment of the invention.

As illustrated in FIG. 24, a surgery-assisting robot 200 including the medical manipulator of the present embodiment is a master/slave type medical system, and includes a manipulation part 250 that is manipulated by an operator OP, a medical manipulator 204 that has a soft insertion part 210 inserted into a patient's P body, a driving part 205 that generates a driving force for operating the medical manipulator 204, a control device 270 that controls the driving part 205, and a display part 260 that displays an image acquired by the medical manipulator 204.

The insertion part 210 is a so-called soft one, and as illustrated in FIG. 25, has a distal end rigid part 211, a bending part 212 that is provided closer to the proximal side than the distal end rigid part 211 and is capable of performing a bending manipulation, and a flexible tube part 213 that is provided closer to the proximal side than the bending part 212 and has flexibility.

A photographing window 211b for capturing a front image is provided in a distal end surface 211a of the distal end rigid part 211. An imaging optical system and an imaging element (not illustrated) are arranged inside the photographing window 211b. Accordingly, the medical manipulator 204 can acquire an image like an endoscope. Additionally, a proximal end of a treatment arm part 230 is attached to a distal end surface 211a of the distal end rigid part 211.

Additionally, the treatment arm part 230 has a multi joint structure, and includes a joint part 232 constituted of a first joint 232A (first unit joint) and a second joint 232B (second unit joint) that are lined up in the longitudinal direction of the treatment arm part 230.

As the first joint 232A and the second joint 232B, for example, the same configuration as that of the first joint 43A and the second joint 43B of the aforementioned second embodiment can be adopted.

A grasping part 237 that is an end effector having a pair of grasping pieces 237a is provided on the forefront side of the joint part 232. A distal end of an operating wire (not illustrated) is connected to the proximal end of each grasping piece 237a. The operating wire is inserted through the joint part 232, extends to the proximal side of the treatment arm part 230, and is coupled to a driving part (not illustrated) in the manipulation part 250.

As illustrated in FIG. 24, the manipulation part 250 has a pair of manipulating arms 252 and 253 attached to a console 251, and a foot switch 254 arranged on a floor surface F. The manipulating arms 252 and 253 have a multi joint structure. The manipulating arm 252 performs a bending manipulation of the bending part at the distal end of the insertion part 210, and the manipulating arm 253 performs a bending manipulation of the treatment arm part 230 provided at the distal end of the medical manipulator 204.

The same position-adjusting part 23 as that of the aforementioned second embodiment is provided between the tubular part 24a provided in the driving part 205, and the same tubular part (not illustrated), at a proximal end of the insertion part 210.

By virtue of such a configuration, the driving part 205, the position-adjusting part 23, the insertion part 210, and the treatment arm part 230 in the surgery-assisting robot 200 constitute the medical manipulator 204 of the present embodiment. Here, the insertion part 210 constitutes an elongated part. The position-adjusting part 23 and a male screw part (not illustrated) provided in the insertion part 210 constitute a wire relaxation mechanism of the present embodiment.

In the present embodiment, the insertion part 210 that is the elongated part is soft. Therefore, the driving wires 55A and 55B (not illustrated), the wire 11 for a first guide, and the wire 12 for a second guide inserted through the insertion part 210 are inserted into a wire sheath within the insertion part 210, and are configured so that the lengths of the wires do not change even if the insertion part is bent.

In this way, the medical manipulator 204 of the present embodiment can operate similarly to the medical manipulator 41 of the aforementioned second embodiment except that the elongated part is soft.

For this reason, the medical manipulator 204 having the joint part 232 can be more efficiently and more easily cleaned.

In addition, a case in which the length of the body part itself is changed by the position-adjusting part has been described as an example, in the description of the aforementioned respective embodiments and respective modification examples. However, the wire relaxation mechanism has only to be extended and retracted so that the driving wire member and the guide wire can be relaxed by changing a fixation position and an engagement position for applying tensions to the driving wire member and the guide wire. The length of the body part itself may not be changed. For example, the driving part may be encapsulated by a member, such as a housing that constitutes a main body-sheathing part that is not moved by the manipulation of the wire relaxation mechanism.

Additionally, although a case where an elongated hole is adopted as a part on which the turning shaft or the like slides has been described as an example, the sliding part may be, for example, a U-shaped slit formed between a side where the turning shaft abuts and turns, and an opposite side end. In this case, the length of the slit is a length such that the turning shaft or the like is not separated when the turning shaft is brought into the relaxation state.

The end effector of the medical manipulator of the invention is not particularly limited if only an effector provided at the distal end of the joint part is provided, and suitable effectors, such as an imaging element and a sensor other than the treatment part, the grasping part, and the like, can be adopted.

Although a case where the extension/retraction elastic length of the wire relaxation mechanism 30 in the drivable state is constant and the length is maintained by the stopper part 29 has been described as an example in the aforementioned respective embodiments and respective modification examples, a configuration in which the extension amount of the wire relaxation mechanism 30 in the drivable state is also possible to change.

In this case, for example, in a case where the driving wire member and the guide wire have elongated by being repeatedly used, it is possible to increase the extension amount of the wire relaxation mechanism 30 by an amount slightly stretching before cleaning when the wire relaxation mechanism 30 is returned to the length in the drivable state like after cleaning.

Accordingly, the driving wire member and guide wire in the drivable state can be stretched again, and their respective tensions can be returned to their initial states.

While preferred embodiments of the invention have been described and illustrated above, it should be understood that these are exemplary of the invention and are not to be considered as limiting. Additions, omissions, substitutions, and other modifications can be made without departing from the spirit and scope of the present invention. Accordingly, the invention is not to be considered as being limited by the foregoing description, and is only limited by the scope of the appended claims.

What is claimed is:

1. A medical manipulator comprising:
an end effector;
a joint part that is provided at an end of the end effector and configured to be operated through turning of a rotating body;
an elongated part that has a longitudinal axis and is connected to an end of the joint part opposite to a side where the end effector is provided;
actuator that is provided on a proximal side of the elongated part and configured to supply a driving force for operating the rotating body;
a driving wire member that is connected at least to the rotating body of the joint part and is stretched between the rotating body and the elongated part; and
a wire relaxation mechanism that is configured to relax the driving wire member by changing the path length of the driving wire member,
wherein the joint part includes a unit joint that is coupled to one end of the elongated part in a direction along the longitudinal axis,
wherein the unit joint includes:
a proximal-side support having a first turning shaft that is provided on the elongated part side and extends in a direction intersecting the longitudinal axis at the one end, and a first guide part that has the first turning shaft as a turning shaft;
a distal-side turning body having a second turning shaft that is provided on the end effector side to face the proximal-side support and extends parallel to the first turning shaft, and a second guide part that has the second turning shaft as a turning shaft; and
a coupling member that is the rotating body that holds the first turning shaft and the second turning shaft, respectively, and is configured to be turnable around the first turning shaft, and
wherein the joint part further includes a guide wire that is connected to or engaged with the proximal-side support of the joint part and the distal-side turning body that is the rotating body, the guide wire having an end fixed to the elongated part, and guiding the turning of the distal-side turning body when the joint part operates.

2. The medical manipulator according to claim 1, wherein the wire relaxation mechanism is arranged at a proximal end of the elongated part, and the driving wire member is encapsulated, and
wherein the path length of the driving wire member between the rotating body and the actuator is changed by extending and retracting the wire relaxation mechanism in a longitudinal direction of the elongated part.

3. The medical manipulator according to claim 2, wherein the wire relaxation mechanism includes:
a male screw part that is provided on the proximal side of the elongated part; and
a position-adjusting part that is disposed between the elongated part and the actuator and has a female screw part corresponding to the male screw part, and
wherein the wire relaxation mechanism is extended and retracted in the longitudinal direction of the elongated part by twisting the position-adjusting part.

4. The medical manipulator according to claim 1, wherein the wire relaxation mechanism further includes a stopper part for fixing the path length of the driving wire member not to be changed.

5. The medical manipulator according to claim 4, wherein the stopper part includes:
a stopper member that is disposed to be movable forward and backward on a movement path relative to the actuator of the elongated part when the wire relaxation mechanism is extended and retracted;
an elastic member that biases the stopper member in a direction in which the stopper member advances to the movement path; and
a manipulation part that is configured to release the biasing of the elastic member.

6. The medical manipulator according to claim 1, wherein the driving wire member is wound around and connected to the rotating body, and
wherein the distance between the periphery of the rotating body and the driving wire member increases when the driving wire member is relaxed by the wire relaxation mechanism.

7. The medical manipulator according to claim 1, wherein the first guide part further includes a first pulley,
wherein the second guide part further includes a second pulley that is configured to abut against or engage with the first guide part, and is configured to guide rolling of the end effector along the track of the first guide part, and
wherein the first pulley is configured to guide rolling of the second pulley centered on the first turning shaft.

8. The medical manipulator according to claim 1, wherein the coupling member is capable of changing an inter-axial distance between the first turning shaft and the second turning shaft to the state of a first inter-axial distance at which the first guide part and the second guide part abut against or engage with each other and the state of a second inter-axial distance at which the inter-axial distance is longer than the first inter-axial distance,
wherein the guide wire is wound around the distal-side turning body and the proximal-side support so that a tension is generated in the state of the first inter-axial distance and the guide wire is relaxed in the state of the second inter-axial distance, and
wherein the wire relaxation mechanism adjusts the relative positions of the elongated part and the actuator, thereby forming the state of the second inter-axial distance to relax at least the guide wire.

9. The medical manipulator according to claim 1, wherein the guide wire is connected or engaged such that the guide wire cannot be separated from at least one of the actuator and the distal-side turning body.

10. The medical manipulator according to claim 1, wherein the guide wire is connected or engaged at a predetermined position of at least one of the actuator and the distal-side turning body.

11. The medical manipulator according to claim 1, wherein the first guide part and the second guide part are constituted of a set of gear members,
wherein a first wire insertion part capable of stretching the guide wire between axial centers is formed in the first turning shaft,
wherein a second wire insertion part capable of stretching the guide wire between axial centers is formed in the second turning shaft, and wherein the guide wire is inserted through the first wire insertion part and the second wire insertion part and is connected to or engaged with the actuator and the distal-side turning body.

12. The medical manipulator according to claim 1,
wherein the coupling member includes a fixing pulley that has a pulley groove for winding the driving wire member on a circumference coaxial with the first turning shaft, and
wherein the actuator includes a driving pulley that engages with the driving wire member and moves the driving wire member forward and backward in the direction along the longitudinal axis.

13. The medical manipulator according to any one of claim 1,
wherein the joint part includes a first unit joint and a second unit joint that are coupled to one end of the elongated part in the direction along the longitudinal axis,
wherein the first unit joint is coupled to the one end of the elongated part, and the second unit joint couples the distal-side turning body of the first unit joint and the end effector, and
wherein the first unit joint and the second unit joint are coupled together in a positional relationship in which axis directions of the first turning shaft and the second turning shaft of the second unit joint are orthogonal at positions twisted from axis directions of the first turning shaft and the second turning shaft of the first unit joint.

14. A medical manipulator comprising:
an end effector;
a joint part that is provided at an end of the end effector and configured to be operated through turning of a rotating body;
an elongated part that has a longitudinal axis and is connected to an end of the joint part opposite to a side where the end effector is provided;
an actuator that is provided on a proximal side of the elongated part and configured to supply a driving force for operating the rotating body;
a driving wire member that is connected at least to the rotating body of the joint part and is stretched between the rotating body and the elongated part; and
a wire relaxation mechanism that is configured to relax the driving wire member by changing the path length of the driving wire member,
wherein the wire relaxation mechanism further includes a stopper part for fixing the path length of the driving wire member not to be changed, and
wherein the stopper part includes:
a stopper member that is disposed to be movable forward and backward on a movement path relative to the actuator of the elongated part when the wire relaxation mechanism is extended and retracted;
an elastic member that biases the stopper member in a direction in which the stopper member advances to the movement path; and
a manipulation part that is configured to release the biasing of the elastic member.

15. The medical manipulator according to claim 14,
wherein the wire relaxation mechanism is arranged at a proximal end of the elongated part, and the driving wire member is encapsulated, and
wherein the path length of the driving wire member between the rotating body and the actuator is changed by extending and retracting the wire relaxation mechanism in a longitudinal direction of the elongated part.

16. The medical manipulator according to claim 15,
wherein the wire relaxation mechanism includes:
a male screw part that is provided on the proximal side of the elongated part; and
a position-adjusting part that is disposed between the elongated part and the actuator and has a female screw part corresponding to the male screw part, and
wherein the wire relaxation mechanism is extended and retracted in the longitudinal direction of the elongated part by twisting the position-adjusting part.

17. The medical manipulator according to claim 14,
wherein the driving wire member is wound around and connected to the rotating body, and
wherein the distance between the periphery of the rotating body and the driving wire member increases when the driving wire member is relaxed by the wire relaxation mechanism.

18. The medical manipulator according to claim 14,
wherein the joint part includes a unit joint that is coupled to one end of the elongated part in a direction along the longitudinal axis,
wherein the unit joint includes:
a proximal-side support having a first turning shaft that is provided on the elongated part side and extends in a direction intersecting the longitudinal axis at the one end, and a first guide part that has the first turning shaft as a turning shaft;
a distal-side turning body having a second turning shaft that is provided on the end effector side to face the proximal-side support and extends parallel to the first turning shaft, and a second guide part that has the second turning shaft as a turning shaft; and
a coupling member that is the rotating body that holds the first turning shaft and the second turning shaft, respectively, and is configured to be turnable around the first turning shaft, and
wherein the joint part further includes a guide wire that is connected to or engaged with the proximal-side support of the joint part and the distal-side turning body that is the rotating body, the guide wire having an end fixed to the elongated part, and guiding the turning of the distal-side turning body when the joint part operates.

* * * * *